(12) United States Patent
Selkee et al.

(10) Patent No.: US 11,850,051 B2
(45) Date of Patent: Dec. 26, 2023

(54) MAPPING GRID WITH HIGH DENSITY ELECTRODE ARRAY

(71) Applicant: Biosense Webster (Israel) Ltd., Yokneam (IL)

(72) Inventors: Thomas Selkee, Irwindale, CA (US); Keshava Datta, Chino Hills, CA (US); Thanh Nguyen, El Monte, CA (US); Anand Rao, Tustin, CA (US); Rajesh Pendekanti, Irwindale, CA (US); Meir Bar-Tal, Haifa (IL); Ricardo Padilla, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 679 days.

(21) Appl. No.: 16/830,011

(22) Filed: Mar. 25, 2020

(65) Prior Publication Data
US 2020/0345262 A1    Nov. 5, 2020

Related U.S. Application Data

(60) Provisional application No. 62/841,154, filed on Apr. 30, 2019.

(51) Int. Cl.
*A61B 5/287*   (2021.01)
*A61B 5/00*   (2006.01)
(Continued)

(52) U.S. Cl.
CPC ............ *A61B 5/287* (2021.01); *A61B 5/283* (2021.01); *A61B 5/6856* (2013.01);
(Continued)

(58) Field of Classification Search
CPC ....... A61B 5/062; A61B 5/287; A61B 5/6856; A61B 5/6858
See application file for complete search history.

(56) References Cited

U.S. PATENT DOCUMENTS

| 4,699,147 A | 10/1987 | Chilson et al. |
| 4,940,064 A | 7/1990 | Desai |

(Continued)

FOREIGN PATENT DOCUMENTS

| CN | 102665586 A | 9/2012 |
| CN | 102892453 A | 1/2013 |

(Continued)

OTHER PUBLICATIONS

Extended European Search Report dated Sep. 21, 2020, from corresponding EP Application No. 20172013.3.

(Continued)

*Primary Examiner* — Eun Hwa Kim
(74) *Attorney, Agent, or Firm* — Troutman Pepper Hamilton Sanders LLP

(57) ABSTRACT

A catheter is described with an end effector having densely arrayed electrodes on three loops which are arrayed in various planar configurations when the end effector is unconstrained. The end effector has first, second and third loop members, each loop member includes two spines and a connector that connects the two spines to define a loop extending away from a tubular member of the catheter such that the first, second and third loop members are configured so that each connector of each of the first, second and third loop members is in contact with only one connector of the adjacent loop member.

17 Claims, 19 Drawing Sheets

(51) Int. Cl.
*A61B 18/14* (2006.01)
*A61B 5/283* (2021.01)
*A61B 18/00* (2006.01)

(52) U.S. Cl.
CPC .................. *A61B 18/1492* (2013.01); *A61B 2018/00577* (2013.01); *A61B 2018/00839* (2013.01)

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,443,489 A * | 8/1995 | Ben-Haim | A61B 5/06 607/122 |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,558,091 A | 9/1996 | Acker et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,630,918 A | 5/1997 | Takahara et al. | |
| 5,681,280 A | 10/1997 | Rusk et al. | |
| 5,702,438 A | 12/1997 | Avitall | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,782,899 A | 7/1998 | Imran | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,944,022 A | 8/1999 | Nardella et al. | |
| 5,964,757 A | 10/1999 | Ponzi | |
| 5,968,040 A | 10/1999 | Swanson et al. | |
| 5,983,126 A | 11/1999 | Wittkampf | |
| 6,014,579 A | 1/2000 | Pomeranz et al. | |
| 6,014,590 A | 1/2000 | Whayne et al. | |
| 6,071,280 A | 6/2000 | Edwards et al. | |
| 6,071,282 A * | 6/2000 | Fleischman | A61B 18/1492 606/41 |
| 6,119,030 A | 9/2000 | Morency | |
| 6,123,699 A | 9/2000 | Webster, Jr. | |
| 6,142,993 A | 11/2000 | Whayne et al. | |
| 6,171,277 B1 | 1/2001 | Ponzi | |
| 6,172,499 B1 | 1/2001 | Ashe | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,216,043 B1 | 4/2001 | Swanson et al. | |
| 6,216,044 B1 | 4/2001 | Kordis | |
| 6,245,068 B1 * | 6/2001 | Olson | A61L 31/10 606/41 |
| 6,267,746 B1 | 7/2001 | Bumbalough | |
| 6,415,187 B1 | 7/2002 | Kuzma et al. | |
| 6,428,537 B1 | 8/2002 | Swanson et al. | |
| 6,445,864 B2 | 9/2002 | Jiang et al. | |
| 6,522,932 B1 | 2/2003 | Kuzma | |
| 6,574,492 B1 | 6/2003 | Ben-Haim et al. | |
| 6,584,345 B2 | 6/2003 | Govari | |
| 6,590,963 B2 | 7/2003 | Mohammadian | |
| 6,600,948 B2 | 7/2003 | Ben-Haim et al. | |
| 6,658,302 B1 | 12/2003 | Kuzma et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,788,967 B2 | 9/2004 | Ben-Haim et al. | |
| 6,837,886 B2 | 1/2005 | Collins et al. | |
| 6,866,662 B2 | 3/2005 | Fuimaono et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,099,712 B2 | 8/2006 | Fuimaono et al. | |
| 7,149,563 B2 | 12/2006 | Fuimaono et al. | |
| 7,155,270 B2 | 12/2006 | Solis et al. | |
| 7,255,695 B2 | 8/2007 | Falwell et al. | |
| 7,257,434 B2 | 8/2007 | Fuimaono et al. | |
| 7,257,435 B2 | 8/2007 | Plaza | |
| 7,399,299 B2 | 7/2008 | Daniel et al. | |
| 7,412,274 B2 | 8/2008 | Mejia | |
| 7,429,261 B2 | 9/2008 | Kunis et al. | |
| 7,522,950 B2 | 4/2009 | Fuimaono et al. | |
| 7,536,218 B2 | 5/2009 | Govari et al. | |
| RE41,334 E | 5/2010 | Beatty et al. | |
| 7,756,567 B2 | 7/2010 | Kudu Valli et al. | |
| 7,846,157 B2 | 12/2010 | Kozel | |
| 7,848,787 B2 | 12/2010 | Osadchy | |
| 7,869,865 B2 | 1/2011 | Govari et al. | |
| 7,930,018 B2 | 4/2011 | Harlev et al. | |
| 8,007,495 B2 | 8/2011 | McDANIEL et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,206,404 B2 | 6/2012 | De La Rama et al. | |
| 8,224,416 B2 | 7/2012 | De La Rama et al. | |
| 8,235,988 B2 | 8/2012 | Davis et al. | |
| 8,271,099 B1 | 9/2012 | Swanson | |
| 8,273,084 B2 | 9/2012 | Kunis et al. | |
| 8,346,339 B2 | 1/2013 | Kordis et al. | |
| 8,391,947 B2 | 3/2013 | Urman et al. | |
| 8,435,232 B2 | 5/2013 | Aeby et al. | |
| 8,447,377 B2 | 5/2013 | Harlev et al. | |
| 8,456,182 B2 | 6/2013 | Bar-Tal et al. | |
| 8,480,669 B2 | 7/2013 | Pappone et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,571,626 B2 | 10/2013 | Lau et al. | |
| 8,603,069 B2 | 12/2013 | Selkee | |
| 8,712,550 B2 | 4/2014 | Grunewald | |
| 8,715,279 B2 | 5/2014 | De La Rama et al. | |
| 8,734,440 B2 | 5/2014 | Wu | |
| 8,744,599 B2 | 6/2014 | Tegg | |
| 8,755,861 B2 | 6/2014 | Harlev et al. | |
| 8,764,742 B2 | 7/2014 | Pappone et al. | |
| 8,790,341 B2 | 7/2014 | Pappone et al. | |
| 8,825,130 B2 | 9/2014 | Just et al. | |
| 8,827,910 B2 | 9/2014 | De La Rama et al. | |
| 8,906,011 B2 | 12/2014 | Gelbart et al. | |
| 8,945,120 B2 | 2/2015 | McDaniel et al. | |
| 8,974,454 B2 | 3/2015 | De La Rama et al. | |
| 8,979,837 B2 | 3/2015 | De La Rama et al. | |
| 8,979,839 B2 | 3/2015 | De La Rama et al. | |
| 9,037,264 B2 | 5/2015 | Just et al. | |
| 9,044,245 B2 | 6/2015 | Condie et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |

(56) References Cited

U.S. PATENT DOCUMENTS

| | | |
|---|---|---|
| 9,480,491 B1 | 11/2016 | Dostal et al. |
| 9,486,282 B2 | 11/2016 | Solis |
| 9,554,718 B2 | 1/2017 | Bar-Tal et al. |
| 9,561,075 B2 | 2/2017 | Pappone et al. |
| D782,686 S | 3/2017 | Werneth et al. |
| 9,585,588 B2 | 3/2017 | Marecki et al. |
| 9,597,036 B2 | 3/2017 | Aeby et al. |
| 9,642,675 B2 | 5/2017 | Werneth et al. |
| 9,687,297 B2 | 6/2017 | Just et al. |
| 9,693,733 B2 | 7/2017 | Altmann et al. |
| 9,724,492 B2 | 8/2017 | De La Rama et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,820,664 B2 | 11/2017 | Hoitink et al. |
| 9,833,161 B2 | 12/2017 | Govari |
| 9,833,608 B2 | 12/2017 | Masson |
| 9,848,795 B2 | 12/2017 | Marecki et al. |
| 9,877,781 B2 | 1/2018 | Grasse et al. |
| 9,894,756 B2 | 2/2018 | Weinkam et al. |
| 9,895,073 B2 | 2/2018 | Solis |
| 9,907,480 B2 | 3/2018 | Basu et al. |
| 9,907,609 B2 | 3/2018 | Cao et al. |
| 9,949,656 B2 | 4/2018 | Wu et al. |
| 9,962,224 B2 | 5/2018 | Pappone et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,039,598 B2 | 8/2018 | De La Rama et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,220,187 B2 | 3/2019 | De La Rama et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,433,903 B2 | 10/2019 | Pappone et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,729 B2 | 12/2019 | De La Rama et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,576,244 B2 | 3/2020 | De La Rama et al. |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,842,990 B2 | 11/2020 | De La Rama et al. |
| 10,857,349 B2 | 12/2020 | De La Rama et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2004/0199200 A1 | 10/2004 | Teague et al. |
| 2004/0210121 A1 | 10/2004 | Fuimaono et al. |
| 2004/0254572 A1 | 12/2004 | McIntyre et al. |
| 2005/0159741 A1 | 7/2005 | Paul |
| 2006/0100669 A1 | 5/2006 | Fuimaono et al. |
| 2007/0093806 A1 | 4/2007 | Desai et al. |
| 2007/0255273 A1 | 11/2007 | Fernandez et al. |
| 2007/0276212 A1 | 11/2007 | Fuimaono et al. |
| 2008/0249463 A1 | 10/2008 | Pappone et al. |
| 2008/0249522 A1 | 10/2008 | Pappone et al. |
| 2008/0294158 A1 | 11/2008 | Pappone et al. |
| 2009/0012517 A1 | 1/2009 | De La Rama et al. |
| 2009/0198300 A1 | 8/2009 | Zhang et al. |
| 2010/0152731 A1 | 6/2010 | De La Rama et al. |
| 2010/0174177 A1 | 7/2010 | Wu |
| 2010/0286684 A1 | 11/2010 | Hata et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0288392 A1 | 11/2011 | De La Rama et al. |
| 2011/0301597 A1 | 12/2011 | McDaniel et al. |
| 2011/0313417 A1 | 12/2011 | De La Rama et al. |
| 2012/0010490 A1 | 1/2012 | Kauphusman et al. |
| 2012/0130217 A1 | 5/2012 | Kauphusman et al. |
| 2012/0130218 A1 | 5/2012 | Kauphusman et al. |
| 2012/0172859 A1 | 7/2012 | Condie |
| 2012/0239031 A1 | 9/2012 | Pappone et al. |
| 2012/0265130 A1 | 10/2012 | De La Rama et al. |
| 2012/0296232 A1 | 11/2012 | Ng |
| 2013/0085479 A1 | 4/2013 | De La Rama et al. |
| 2013/0090651 A1 | 4/2013 | Smith |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0274582 A1 | 10/2013 | Afonso |
| 2013/0296852 A1 | 11/2013 | Madjarov et al. |
| 2013/0310825 A1 | 11/2013 | Pappone et al. |

(56) References Cited

U.S. PATENT DOCUMENTS

| | | |
|---|---|---|
| 2013/0338467 A1 | 12/2013 | Grasse et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0194716 A1 | 7/2014 | Diep et al. |
| 2014/0200639 A1 | 7/2014 | De La Rama |
| 2014/0207136 A1 | 7/2014 | De La Rama et al. |
| 2014/0257069 A1 | 9/2014 | Eliason et al. |
| 2014/0276712 A1 | 9/2014 | Mallin et al. |
| 2014/0296902 A1 | 10/2014 | Andre |
| 2014/0303619 A1 | 10/2014 | Pappone et al. |
| 2014/0309512 A1 | 10/2014 | Govari et al. |
| 2014/0316496 A1 | 10/2014 | Masson et al. |
| 2014/0330269 A1 | 11/2014 | Pappone et al. |
| 2014/0343546 A1 | 11/2014 | De La Rama et al. |
| 2015/0011991 A1 | 1/2015 | Buysman et al. |
| 2015/0045863 A1 | 2/2015 | Litscher et al. |
| 2015/0105645 A1 | 4/2015 | Subramaniam et al. |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0209547 A1 | 7/2015 | De La Rama et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2015/0351652 A1 | 12/2015 | Marecki et al. |
| 2015/0374252 A1 | 12/2015 | de la Rama et al. |
| 2016/0081746 A1 | 3/2016 | Solis |
| 2016/0113709 A1 | 4/2016 | Maor |
| 2016/0143588 A1* | 5/2016 | Hoitink ............... A61B 5/6859 600/374 |
| 2016/0183877 A1 | 6/2016 | Williams et al. |
| 2016/0213916 A1 | 7/2016 | De La Rama |
| 2016/0228062 A1 | 8/2016 | Altmann et al. |
| 2016/0242667 A1 | 8/2016 | Fay et al. |
| 2016/0278853 A1 | 9/2016 | Ogle et al. |
| 2016/0302858 A1 | 10/2016 | Bencini |
| 2016/0317093 A1 | 11/2016 | Berenfeld et al. |
| 2016/0338770 A1 | 11/2016 | Bar-Tal et al. |
| 2016/0374753 A1* | 12/2016 | Wu ............... A61B 5/287 606/41 |
| 2017/0000365 A1 | 1/2017 | Wu et al. |
| 2017/0027638 A1 | 2/2017 | Solis |
| 2017/0035497 A1 | 2/2017 | Nagale et al. |
| 2017/0042449 A1 | 2/2017 | Deno et al. |
| 2017/0049348 A1 | 2/2017 | Deno et al. |
| 2017/0049349 A1 | 2/2017 | Sallee et al. |
| 2017/0065227 A1 | 3/2017 | Marrs et al. |
| 2017/0065341 A1 | 3/2017 | Pappone et al. |
| 2017/0071494 A1 | 3/2017 | Solis et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0105796 A1 | 4/2017 | Pappone et al. |
| 2017/0112404 A1 | 4/2017 | de la Rama et al. |
| 2017/0112405 A1 | 4/2017 | Sterrett et al. |
| 2017/0143227 A1 | 5/2017 | Marecki et al. |
| 2017/0156790 A1 | 6/2017 | Aujla |
| 2017/0165000 A1 | 6/2017 | Basu et al. |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0251978 A1 | 9/2017 | Rodrigo Bort et al. |
| 2017/0265812 A1 | 9/2017 | Williams et al. |
| 2017/0273738 A1 | 9/2017 | Wu |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319269 A1 | 11/2017 | Oliverius et al. |
| 2017/0332970 A1 | 11/2017 | Aujla |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2017/0354797 A1 | 12/2017 | De La Rama et al. |
| 2017/0367756 A1 | 12/2017 | Sliwa et al. |
| 2018/0008203 A1 | 1/2018 | Iyun et al. |
| 2018/0028084 A1 | 2/2018 | Williams et al. |
| 2018/0042667 A1* | 2/2018 | Pappone ............... A61F 7/12 |
| 2018/0049803 A1 | 2/2018 | Solis |
| 2018/0050190 A1 | 2/2018 | Masson |
| 2018/0055563 A1 | 3/2018 | Shetake et al. |
| 2018/0056038 A1 | 3/2018 | Aujla |
| 2018/0070845 A1 | 3/2018 | Hoitink et al. |
| 2018/0085064 A1 | 3/2018 | Auerbach et al. |
| 2018/0116539 A1 | 5/2018 | Olson et al. |
| 2018/0132749 A1 | 5/2018 | Govari et al. |
| 2018/0137687 A1 | 5/2018 | Katz et al. |
| 2018/0160978 A1 | 6/2018 | Cohen et al. |
| 2018/0168511 A1 | 6/2018 | Hall et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0099585 A1 | 4/2019 | De La Rama et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0192221 A1 | 6/2019 | Pappone et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0275291 A2 | 9/2019 | De et al. |
| 2019/0282116 A1 | 9/2019 | Olson |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0038103 A1 | 2/2020 | Pappone et al. |
| 2020/0046421 A1 | 2/2020 | Govari |

(56) References Cited

U.S. PATENT DOCUMENTS

| | | |
|---|---|---|
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0138378 A1 | 5/2020 | De La Rama et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206456 A1 | 7/2020 | De La Rama et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0297996 A1 | 9/2020 | De La Rama et al. |
| 2020/0305726 A1 | 10/2020 | Salvestro et al. |
| 2020/0305946 A1 | 10/2020 | DeSimone et al. |
| 2020/0330752 A1 | 10/2020 | De La Rama et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 103220994 A | 7/2013 |
| CN | 103298392 A | 9/2013 |
| CN | 102892453 B | 4/2015 |
| CN | 104968261 A | 10/2015 |
| CN | 102665586 B | 3/2016 |
| CN | 103298392 B | 8/2016 |
| CN | 104968261 B | 5/2019 |
| CN | 111248993 A | 6/2020 |
| CN | 111248996 A | 6/2020 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2166936 A1 | 3/2010 |
| EP | 2173426 A1 | 4/2010 |
| EP | 2166936 A4 | 7/2010 |
| EP | 2173426 A4 | 7/2010 |
| EP | 2429436 A1 | 3/2012 |
| EP | 2470101 A1 | 7/2012 |
| EP | 2544749 A1 | 1/2013 |
| EP | 2568906 A1 | 3/2013 |
| EP | 2470101 A4 | 6/2013 |
| EP | 2613686 A1 | 7/2013 |
| EP | 2613723 A1 | 7/2013 |
| EP | 2544749 A4 | 10/2013 |
| EP | 2907462 A1 | 2/2014 |
| EP | 2568906 A4 | 5/2014 |
| EP | 2613686 A4 | 7/2014 |
| EP | 2783651 A1 | 10/2014 |
| EP | 2613723 A4 | 4/2015 |
| EP | 2544749 B1 | 8/2015 |
| EP | 2908723 A1 | 8/2015 |
| EP | 2699151 B1 | 11/2015 |
| EP | 2699152 B1 | 11/2015 |
| EP | 2699153 B1 | 12/2015 |
| EP | 2977020 A1 | 1/2016 |
| EP | 2173426 B1 | 4/2016 |
| EP | 2498706 B1 | 4/2016 |
| EP | 3 023 052 A1 | 5/2016 |
| EP | 2429436 B1 | 11/2016 |
| EP | 3 111 872 A1 | 1/2017 |
| EP | 3146926 A1 | 3/2017 |
| EP | 3 184 037 A1 | 6/2017 |
| EP | 2578173 B1 | 6/2017 |
| EP | 2568906 B1 | 8/2017 |
| EP | 2613723 B1 | 10/2017 |
| EP | 2977020 B1 | 11/2017 |
| EP | 3238645 A1 | 11/2017 |
| EP | 2884931 B1 | 1/2018 |
| EP | 3300681 A1 | 4/2018 |
| EP | 2613686 B1 | 9/2018 |
| EP | 2349440 B1 | 8/2019 |
| EP | 3300681 B1 | 11/2019 |
| EP | 3318211 B1 | 12/2019 |
| EP | 3581135 A1 | 12/2019 |
| EP | 2736434 B1 | 2/2020 |
| EP | 2908723 B1 | 3/2020 |
| EP | 3451962 B1 | 3/2020 |
| EP | 2470101 B1 | 5/2020 |
| EP | 3679861 A1 | 7/2020 |
| EP | 3 733 103 A1 | 11/2020 |
| EP | 3738508 A1 | 11/2020 |
| EP | 3738509 A1 | 11/2020 |
| EP | 3972510 A1 | 3/2022 |
| JP | 2012525933 A | 10/2012 |
| JP | 2013516218 A | 5/2013 |
| JP | 2013521892 A | 6/2013 |
| JP | 2014501557 A | 1/2014 |
| JP | 2014502195 A | 1/2014 |
| JP | 5539498 B2 | 7/2014 |
| JP | 2014158957 A | 9/2014 |
| JP | 5753862 B2 | 7/2015 |
| JP | 5778823 B2 | 9/2015 |
| JP | 2015211874 A | 11/2015 |
| JP | 2016502912 A | 2/2016 |
| JP | 6050522 B2 | 12/2016 |
| JP | 6059535 B2 | 1/2017 |
| JP | 6078471 B2 | 2/2017 |
| JP | 2017077479 A | 4/2017 |
| JP | 2017176879 A | 10/2017 |
| JP | 6445509 B2 | 12/2018 |
| JP | 2019030685 A | 2/2019 |
| WO | WO-9421167 A1 | 9/1994 |
| WO | WO-9421169 A1 | 9/1994 |
| WO | WO-9625095 A1 | 8/1996 |

(56) References Cited

FOREIGN PATENT DOCUMENTS

| | | |
|---|---|---|
| WO | WO-9634560 A1 | 11/1996 |
| WO | WO-0182814 A2 | 11/2001 |
| WO | WO-2004087249 A2 | 10/2004 |
| WO | WO-2008124602 A1 | 10/2008 |
| WO | WO-2008124619 A1 | 10/2008 |
| WO | WO-2009006616 A1 | 1/2009 |
| WO | WO-2009023385 A1 | 2/2009 |
| WO | WO-2010129661 A1 | 11/2010 |
| WO | WO-2011081686 A1 | 7/2011 |
| WO | WO-2011112814 A1 | 9/2011 |
| WO | WO-2011159861 A2 | 12/2011 |
| WO | WO-2011159955 A1 | 12/2011 |
| WO | WO-2011159861 A3 | 2/2012 |
| WO | WO-2012068505 A1 | 5/2012 |
| WO | WO-2012071087 A1 | 5/2012 |
| WO | WO-2012100185 A2 | 7/2012 |
| WO | WO-2012068505 A9 | 10/2012 |
| WO | WO-2013052852 A1 | 4/2013 |
| WO | WO-2013162884 A1 | 10/2013 |
| WO | WO-2013173917 A1 | 11/2013 |
| WO | WO-2013176881 A1 | 11/2013 |
| WO | WO 2015095577 A1 | 12/2013 |
| WO | WO 2015130824 A1 | 2/2014 |
| WO | WO 2014113612 A1 | 4/2014 |
| WO | WO 2016001015 A1 | 7/2014 |
| WO | WO-2014176205 A1 | 10/2014 |
| WO | WO-2016019760 A1 | 2/2016 |
| WO | WO-2016044687 A1 | 3/2016 |
| WO | 2017/192712 A1 | 11/2017 |
| WO | WO-2018111600 A1 | 6/2018 |
| WO | WO-2018191149 A1 | 10/2018 |
| WO | WO-2019084442 A1 | 5/2019 |
| WO | WO-2019143960 A1 | 7/2019 |
| WO | WO-2020026217 A1 | 2/2020 |
| WO | WO-2020206328 A1 | 10/2020 |

OTHER PUBLICATIONS

Extended European Search Report dated Dec. 23, 2022, from corresponding EP Application No. 22194801.1.

* cited by examiner

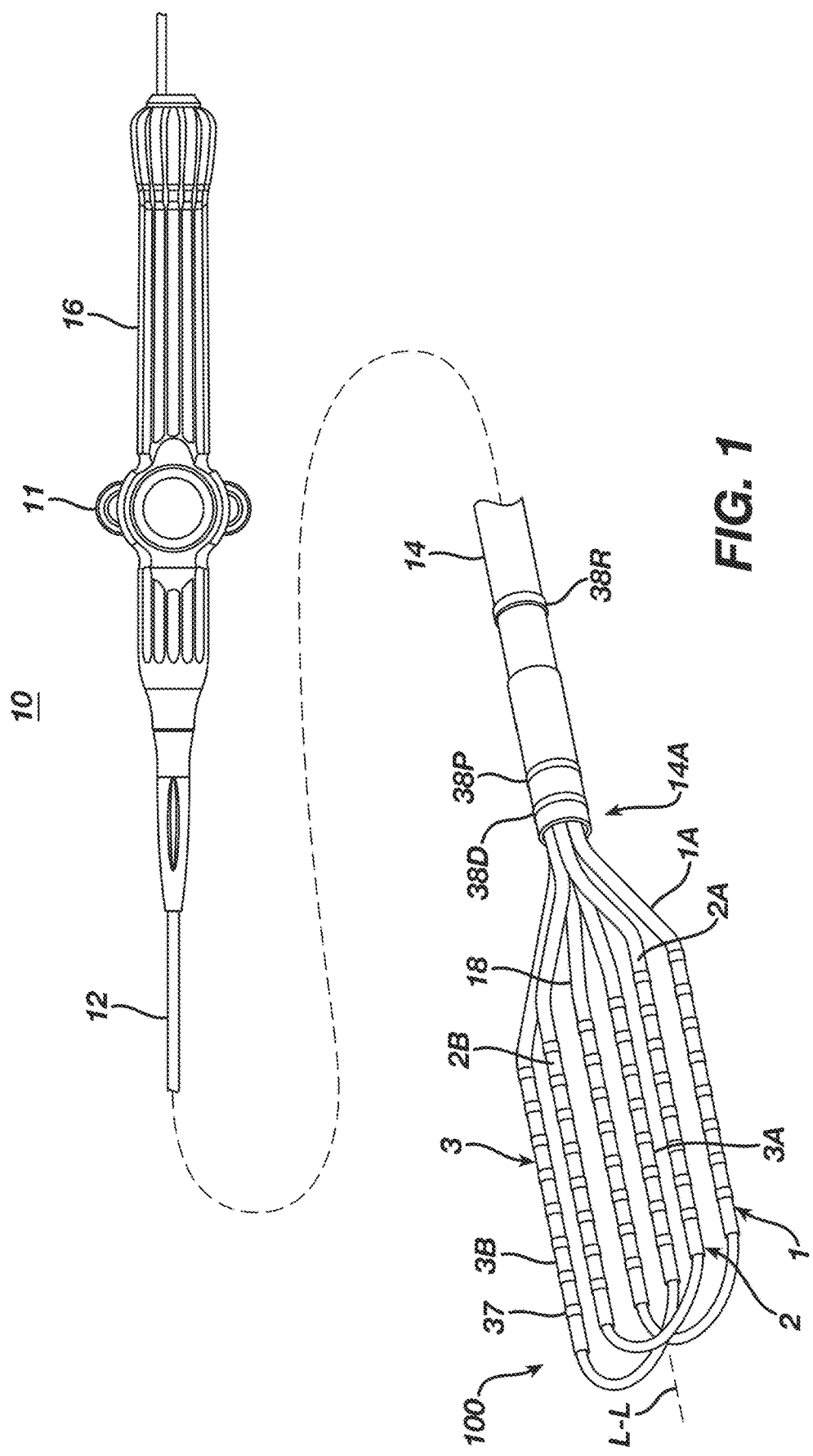

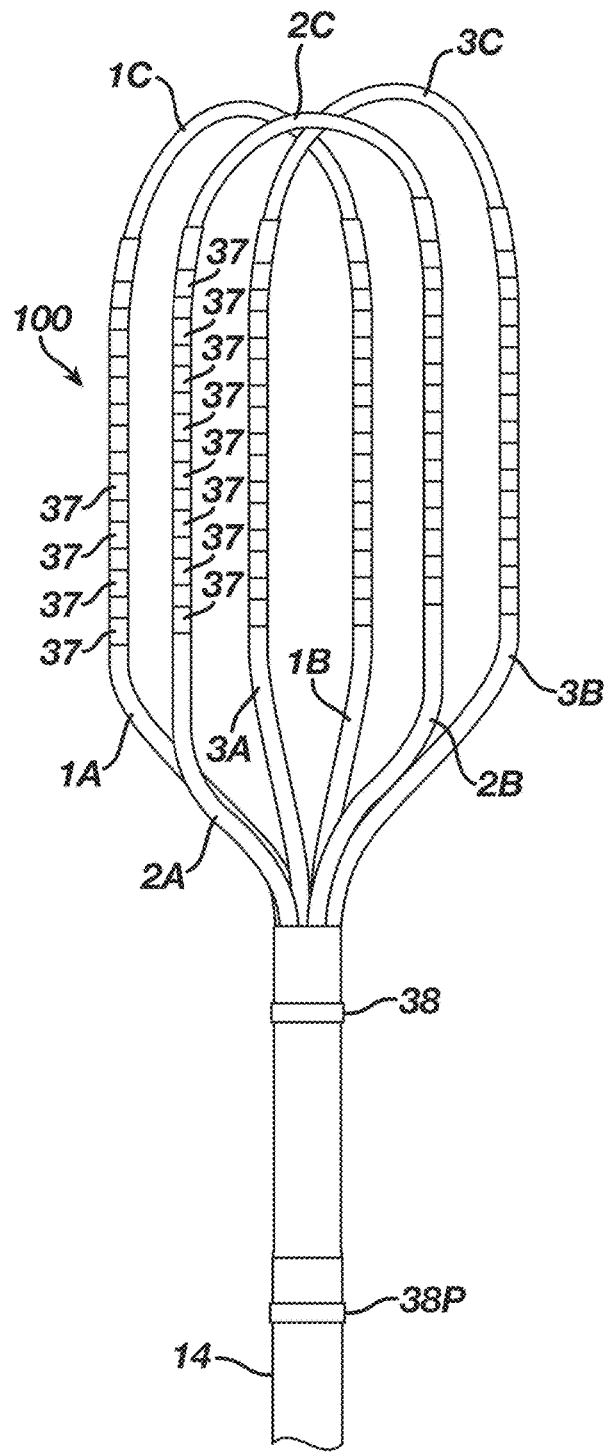
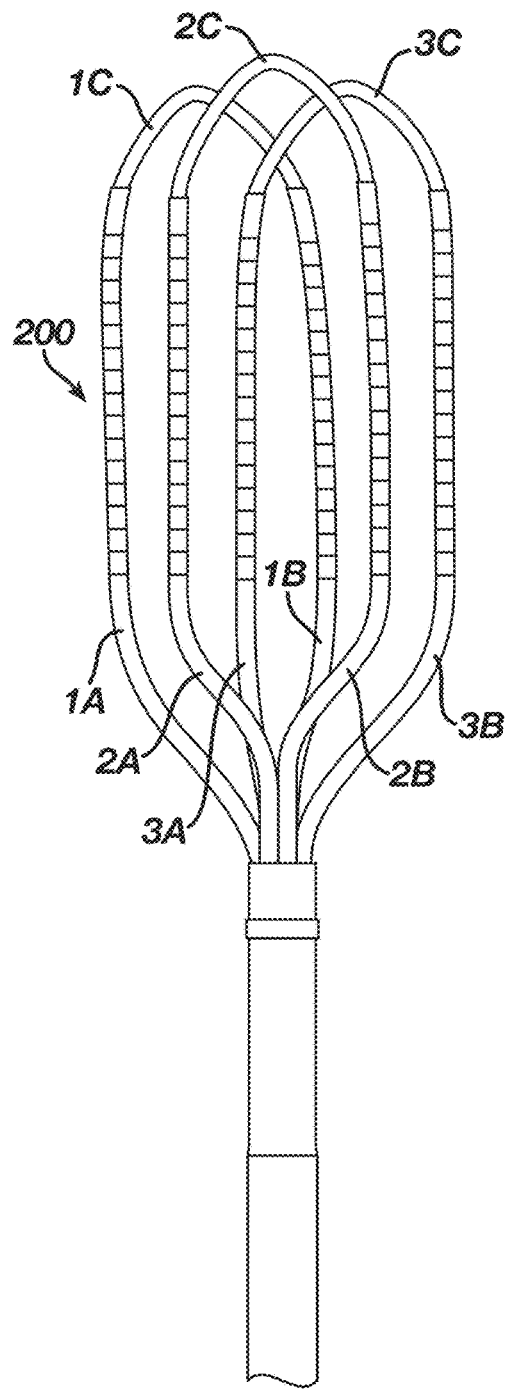
*FIG. 2A*   *FIG. 2B*

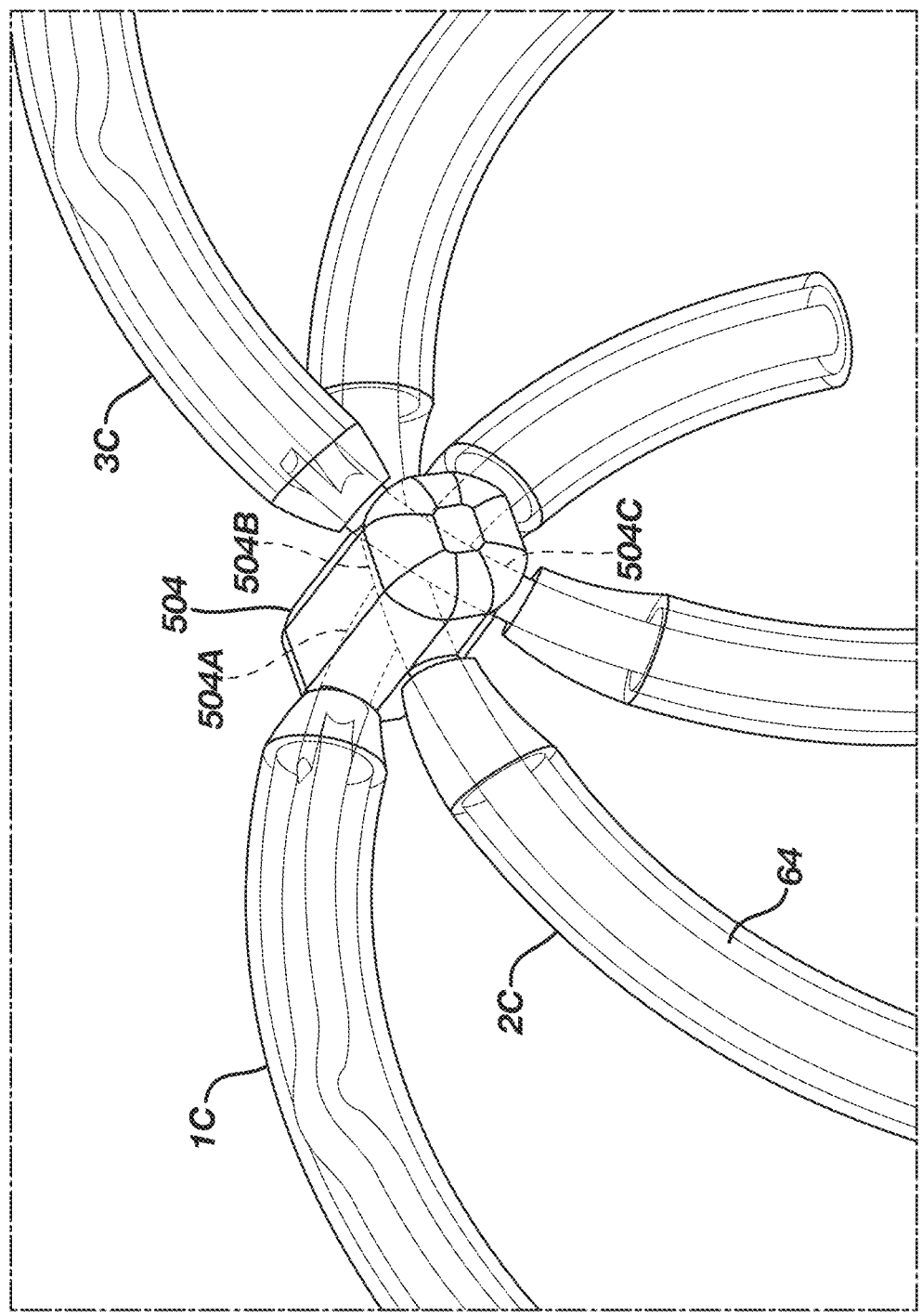

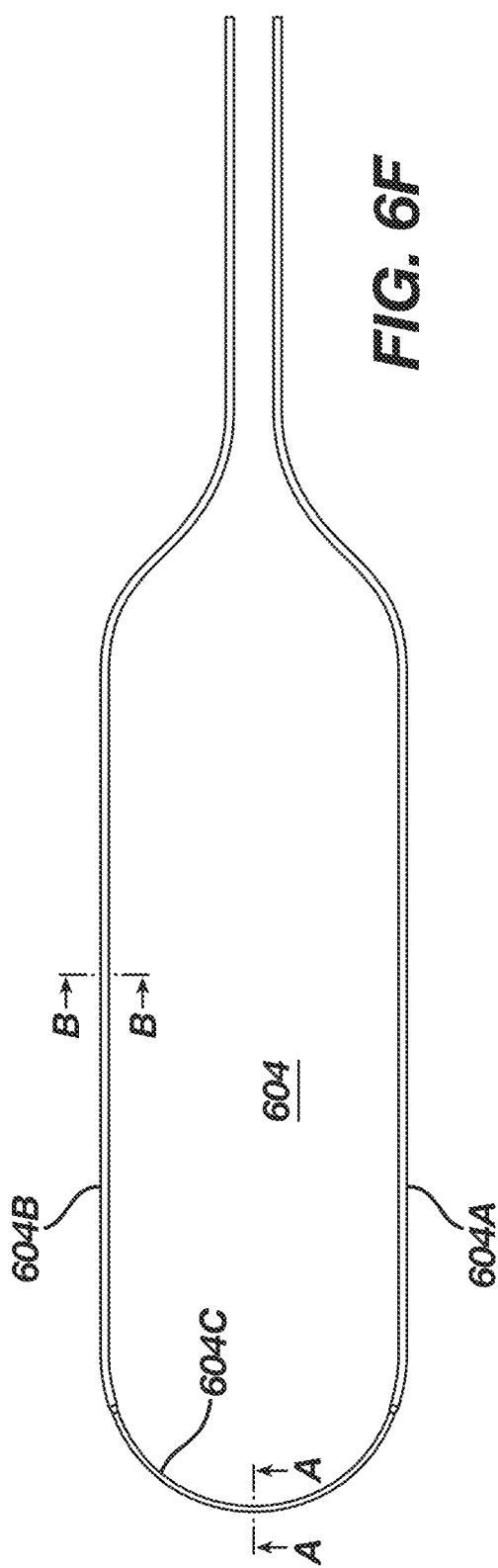
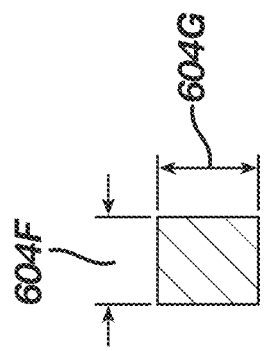
FIG. 6F
FIG. 6G
FIG. 6H

MAPPING GRID WITH HIGH DENSITY ELECTRODE ARRAY

PRIORITY

This application claims the benefits of priority under the Paris Convention as well as 35 USC §§ 119 and 120 to prior filed U.S. provisional patent application Ser. No. 62/841,154, titled as "Mapping Grid with High Density" and filed on Apr. 30, 2019, which priority application is hereby incorporated by reference as if set forth in full herein.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region, for example, one of the atria or one of the ventricles. Regardless of the sources, unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart and acquiring data at a multiplicity of points. These data are then utilized to select the target areas at which ablation is to be performed.

For greater mapping resolution, it is desirable for a mapping catheter to provide very high-density signal maps through the use of a multitude of electrodes sensing electrical activity within a small area, for example, a square centimeter. For mapping within an atria or a ventricle (for example, an apex of a ventricle), it is desirable for a catheter to collect larger amounts of data signals within shorter time spans. It is also desirable for such a catheter to be adaptable to different tissue surfaces, for example, flat, curved, irregular or nonplanar surface tissue and be collapsible for atraumatic advancement and withdrawal through a patient's vasculature.

SUMMARY OF THE DISCLOSURE

Various embodiments described herein allow high density mapping and/or ablation of tissue surface in the heart, including an atria or a ventricle, by virtue of a catheter for electrophysiology applications. The catheter includes a tubular member and an end effector. The tubular member extends along a longitudinal axis from a proximal portion to a distal portion. The end effector is coupled to the distal portion. The end effector includes first, second and third loop members, each loop member includes two spines and a connector that connects the two spines and the first, second and third loop members are configured so that each connector of each of the first, second and third loop members is in contact with only one connector of the adjacent loop member.

In yet another embodiment, a catheter is devised for electrophysiology applications that includes a tubular member and an end effector. The tubular member extends along a longitudinal axis from a proximal portion to a distal portion. The distal portion of the tubular member includes a cross-section disposed about the longitudinal axis. The cross-section intersects first and second orthogonal planes that extend along the longitudinal axis. The cross-section of the distal portion includes first and second openings intersecting the first orthogonal plane and extending along the longitudinal axis, each of the openings configured to receive a puller wire and six apertures are disposed between the first and second openings with four apertures intersecting the second orthogonal plane. Each of the apertures is configured to receive a spine member. The end effector is coupled to the distal portion. The end effector includes three closed-loop members with each loop includes two spines so that six spine members of the three closed-loop members are disposed in the respective six apertures of the distal portion of the catheter.

In another embodiment, a catheter for electrophysiology applications is provided. The catheter includes a tubular member and an end effector. The tubular member extends along a longitudinal axis from a proximal portion to a distal portion. The distal portion of the tubular member has a cross-section disposed about the longitudinal axis where the cross-section intersects first and second orthogonal planes that extend along the longitudinal axis. The cross-section of the distal portion includes first and second openings intersecting the first orthogonal plane and extending along the longitudinal axis, each of the openings configured to receive a puller wire and six apertures disposed between the first and second openings with four apertures intersecting the second orthogonal plane. Each of the apertures is configured to receive a spine member. The end effector is coupled to the distal portion of the tubular member. The end effector includes first, second and third closed-loop members. The end effector has an unrestrained configuration in which: the first closed-loop member includes a first spine connected to a second spine with a first loop connector portion to define a first generally planar surface between the first spine, first loop and second spine such that the first generally planar surface intersects the first and second orthogonal planes, the second closed-loop member includes a third spine connected to a fourth spine with a connector portion to define a second generally planar surface between the third spine, second loop connector portion and fourth spine such that the second generally planar surface intersects the first and second orthogonal planes, and the third closed-loop member includes a fifth spine connected to a sixth spine with a third loop connector portion to define a third generally planar surface that intersects only one of the first and second orthogonal planes.

In yet a further embodiment, a catheter for electrophysiology applications is provided. The catheter includes a tubular member, an end effector and a coupler block. The tubular member extends along a longitudinal axis from a proximal portion to a distal portion. The end effector is coupled to the distal portion. The end effector includes first, second and third loop members, each loop member includes two spines and a connector that connects the two spines. The coupler block connects to each connector of the first, second and third loop members. The coupler is configured to have passages that extends through the coupler block to allow for receipt of each of the respective connectors of the first, second and third loop members.

In another embodiment of a catheter for electrophysiology applications, the catheter includes a tubular member, end effector and a coupler block. The tubular member extends along a longitudinal axis from a proximal portion to a distal portion. The end effector is coupled to the distal portion, the end effector includes first and second loop members, each loop member includes two spines and a connector that connects the two spines. The coupler block connects to each connector of the first and second loop members. The coupler is configured with through passages extending through the coupler block to allow for receipt of each of the respective connectors of the first and second loop members.

In any of the embodiments described earlier, the following features can be combined in various permutations with the embodiments as well as with each other in which each spine may include: an elongated member that provides a structural support for spine, each elongated member configured to have a rectangular cross-section that extends from the distal portion to define a loop; the elongated member comprises a shape memory material; the shape memory material comprises nitinol; the nitinol is cold-worked and crimped during assembly into the apertures of the distal portion; each spine comprises an elongated structure to provide support for each spine, a plurality of electrodes coupled to each elongated structure, the plurality of electrodes spaced at a predetermined spacing with respect to adjacent electrodes on each elongated structure and with respect to electrodes on adjacent elongated structure, and the plurality of electrodes comprises from about 30 to about 100 electrodes total, in which a number of electrodes per elongated structure comprises from about 5 to about 15 electrodes and at least one electrode of the plurality of electrodes that is radiopaque; each spine comprises an elongated structure to provide support for each spine, a plurality of electrodes disposed on each spine, the plurality of electrodes spaced at a predetermined spacing with respect to adjacent electrodes on each spine and with respect to electrodes on adjacent spines, and the plurality of electrodes comprises from about 30 to about 100 electrodes total, in which a number of electrodes per spine comprises from about 5 to about 15 electrodes; each connector for each loop member comprises at least a pair of electrodes disposed on the connector member, the pair of electrodes configured for bi-polar sensing of cardiac signals; a pair of referential electrodes disposed on the distal portion; at least one magnetic sensor disposed proximate the distal portion so that the location of the distal portion can be determined under the magnetic field; at least one impedance location sensor disposed proximate the distal portion of the tubular member to allow a location of the distal portion to be determined based on measured impedance inside a biological subject; the magnetic sensor comprises three single-axis magnetic sensors; each loop member is configured to function as a magnetic sensor so that a location of each loop as referenced to a magnetic field can be determined under the magnetic field; at least one puller wire disposed in the tubular and connected to the distal portion so that the at least one puller wire deflects the distal portion with respect to the longitudinal axis; the at least one puller wire comprises first and second generally parallel puller wires disposed in the tubular member and connected to the distal portion so that the first and second puller wires deflect the distal portion in two directions relative to the longitudinal axis.

In some embodiments, the dragging the distal electrode matrix may include maintaining the parallel arrangement of the matrix and/or maintaining at least portion of the matrix flat on the tissue surface. The dragging the distal electrode matrix may also include maintaining a predetermined relative spacing of the electrodes on the matrix. Notably, "against," "on," "laying," and "lying" are used herein without limiting the relative orientation of the distal electrode matrix and the tissue surface, including, for example, whether one or the other of the matrix and tissue surface is above, below or next to the other.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

FIG. 1 illustrates a catheter from an effector at a distal portion of the catheter to the proximal handle;

FIGS. 2A, 2B and 2C illustrate, respectively, three other variations of the end effector of FIG. 1;

FIGS. 5A, 5B, 5C, 5D, 5E, 5F illustrate various couplers that can be used to ensure that the loop members of the end effector can be maintained in a desired spatial configuration when the end effector is not constrained for a delivery sheath;

FIGS. 6F, 6G and 6H illustrate a generally symmetrical structural backbone of the spines for the second loop member as well as the necessary cross-sections;

MODES OF CARRYING OUT THE INVENTION

Figure 2C:
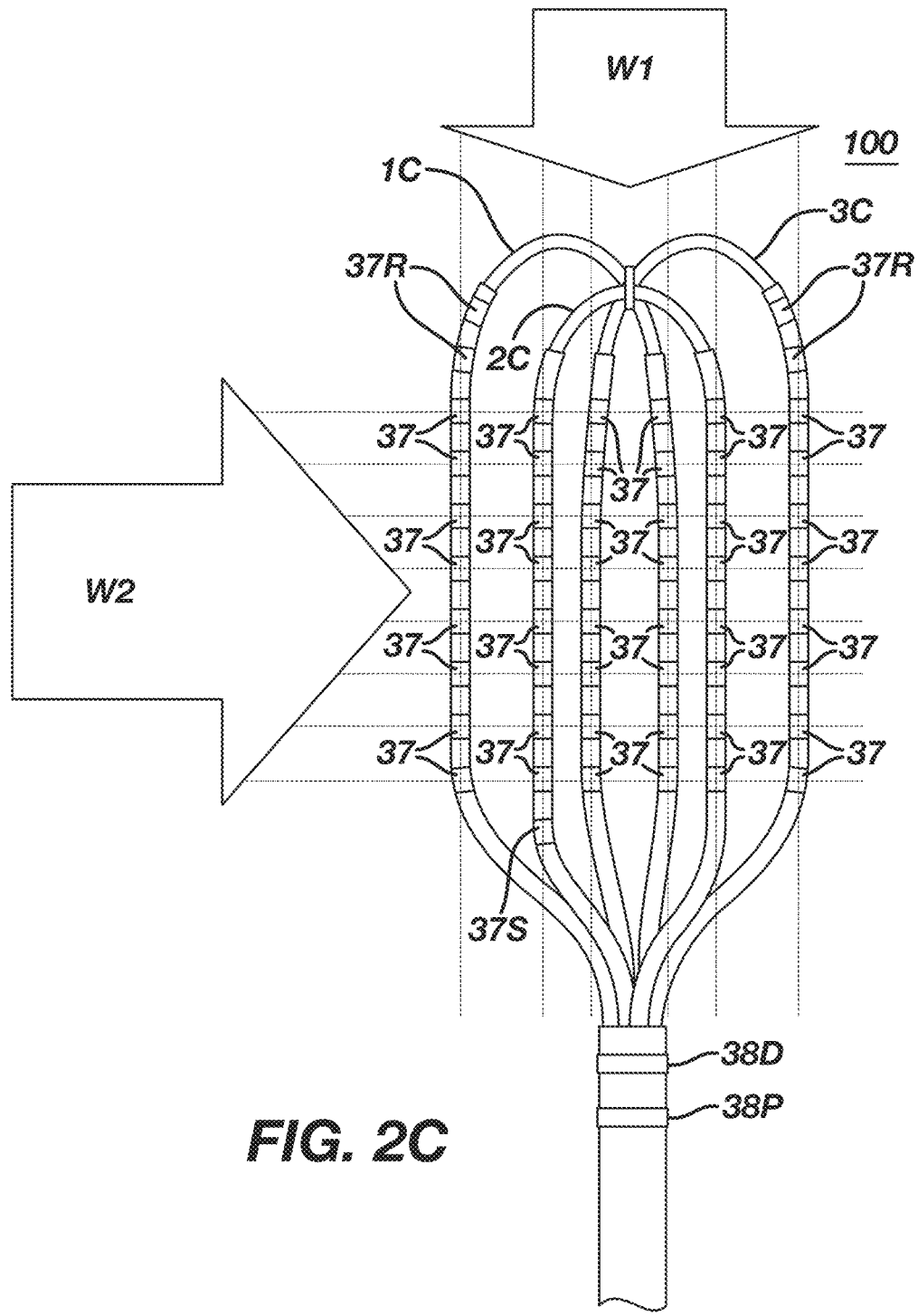

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "proximal" and "distal" are used to reference location of various components with respect to the handle which is designated as the most proximal to a user operating the handle.

As shown in FIG. 1, the catheter 10 comprises an elongated catheter body 12, an intermediate deflection section 14, a distal electrode assembly or end effector 100, and a deflection control handle 16 attached to the proximal end of the catheter body 12. In accordance with a feature of the present invention, the end effector 100 end effector 100 has a plurality of spines 1A, 1B, 2A, 2B, 3A, 3B that generally lie within a common plane akin to a broom having bristles that generally lie within a common plane. The intermediate section is in the form of a tubular member 14 that extends along a longitudinal axis L-L from a proximal portion 12 to a distal portion 14A. Distal electrode 38D and proximal electrode 38P are provided proximate the distal portion 14A so that both electrodes 38D and 38P can cooperate (by masking of a portion of one electrode and masking a different portion on the other electrode) to define a referential electrode (an electrode that is not in contact with tissues). One or more impedance sensing electrode 38R is also provided to allow for location sensing via impedance location sensing technique, as described in U.S. Pat. Nos. 5,944,022; 5,983,126; and 6,445,864, of which a copy is provided in the priority U.S. Provisional Patent Application 62/841,154 and incorporated herein by reference.

Distal portion 14A is coupled to an end effector 100 in FIG. 1. The end effector 100 has first, second and third closed loop members 1, 2, and 3. Each loop member (1, 2 or 3) has two spines (A, B) and a connector (C) that connects the two spines (nA, nB where n represents the spine of one loop). Hence, the first, second and third loop members 1, 2, 3 are configured so that each connector (C) of each of the first, second and third loop members 1, 2, 3 is in contact with only one connector (C) of the adjacent loop members 1, 2, 3. For example, as shown in FIG. 1, spine 1A is connected to spine 1B via connector loop 1C to define first loop member 1; spine 2A is connected to spine 2B via connector loop 2C to define second loop member 2; spine 3A is connected to spine 3B via connector loop 3C to define third loop member 3. Referring to FIG. 2A, only one connector 3C may contact two other connectors 1C and 2C whereas in FIG. 2B, each connector (1C, 2C or 3C) may contact two other connectors (1C contacting connectors 2C and 3C; 2C contacting both connectors 1C and 3C; 3C contacting connectors 2C and 1C). In the alternative embodiment shown in FIG. 2C, the three loops 1, 2 and 3 can be attached via a suture 150 so that the loops maintain their spatial configuration when the end-effector 100 is unconstrained or fully expanded. As will be discussed later, there are 48 electrode 37 disposed in the grid-like configuration with at least four additional electrodes 37R disposed on the connectors 1C, 2C and 3C as well as an additional electrode 37S disposed on the proximal side of the end-effector. Electrode 37R and 37S allows for signal coverage in configuration where the grid electrodes cannot reach desired spatial location. Moreover, the spatial configuration of the three loops allow for the electrode rings 37 to define a grid (dashed lines) so that electrical signals propagating in an orthogonal manner (W1 and W2) are captured with the highest resolution due to the grid (square or rectangular) nature of the end effector 100. FIG. 2F illustrates another embodiment in which additional electrodes 37R are provided through out the entire length of the curved connector loops 1C, 2C and 3C at the distal end of the end effector 100'.

Figure 2D:
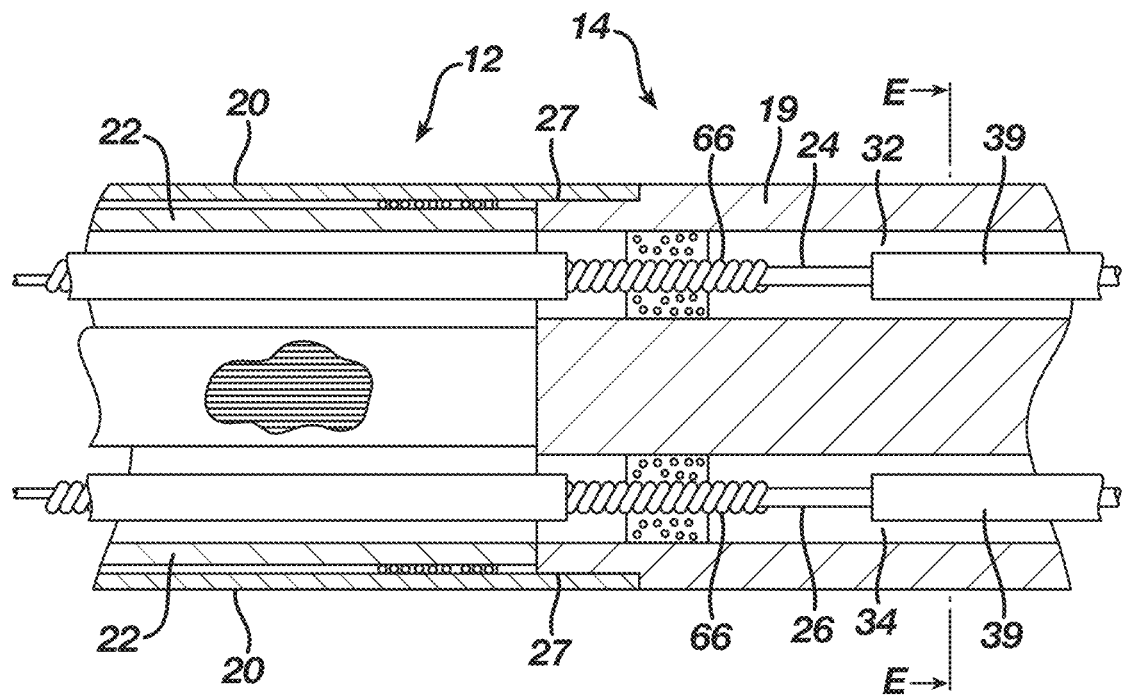
FIGS. 2D and 2E illustrate, respectively, a side sectional view of an intermediate section 14 of the catheter and a sectional view E-E of the intermediate section 14 to show various lumens and components in the lumens.

With reference to FIG. 2D, the catheter body 12 can be an elongated tubular construction having a single axial passage or central lumen 18. The catheter body 12 is flexible, i.e., bendable, but substantially non-compressible along its length. The catheter body 12 can be of any suitable construction and made of any suitable material. In some embodiments, the catheter body 12 comprises an outer wall 20 made of polyurethane or PEBAX. The outer wall 20 may include an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 French, more preferably about 7 French. Likewise, the thickness of the outer wall 20 is not critical but is thin enough so that the central lumen 18 can accommodate at least one puller wire, one or more lead wires, and any other desired wires, cables or tubes. If desired, the inner surface of the outer wall 20 is lined with a stiffening tube 22 to provide improved torsional stability. In some embodiments, the outer wall 20 has an outer diameter of from about 0.090 inch to about 0.94 inch and an inner diameter of from about 0.061 inch to about 0.065 inch.

Figure 2E:
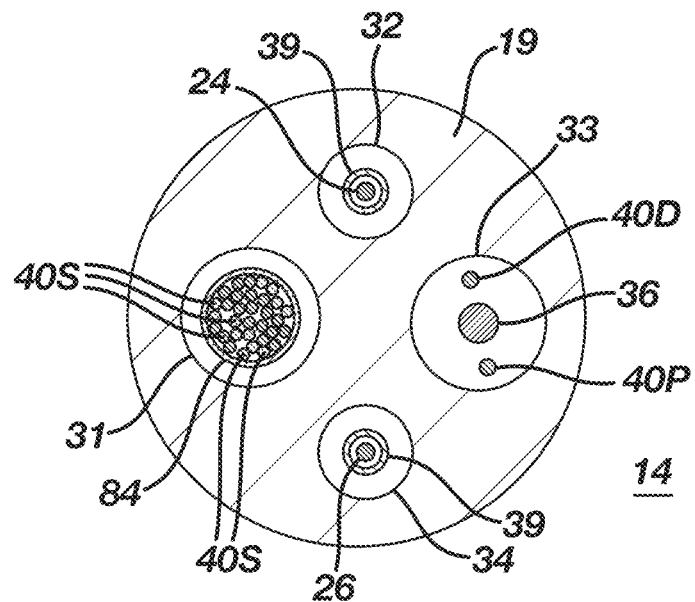
Figure 2F:
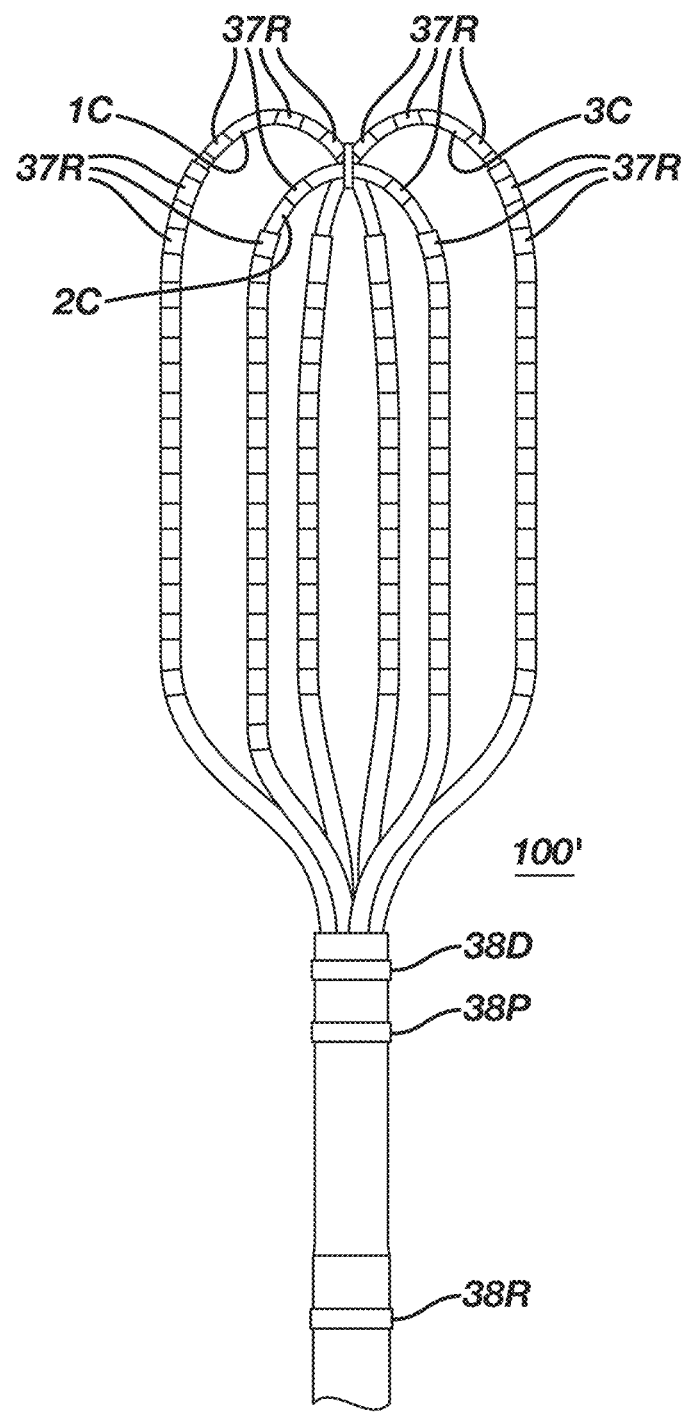
FIG. 2F illustrates another embodiment in which additional electrodes 37R are provided throughout the entire length of the curved connector loops 1C, 2C and 3C at the distal end of the end effector 100'.

As shown in FIGS. 2D and 2E, the intermediate section 14 comprises a shorter section of tubing 19 having multiple lumens, for example, four off-axis lumens 31, 32, 33 and 34. The first lumen 31 carries a plurality of lead wires 40S for ring electrodes 37 carried on the spines 1A, 1B, 2A, 2B, 3A, 3B. The second lumen 32 carries a first puller wire 24. The third lumen 33 carries a cable 36 for an electromagnetic position sensor 42 and a plurality of lead wires 40D and 40P for distal and proximal ring electrodes 38D and 38P carried on the catheter proximally of the end effector 100. Electromagnetic location sensing technique is described in U.S. Pat. Nos. 5,391,199; 5,443,489; 5,558,091; 6,172,499; 6,590,963; and 6,788,967. The magnetic location sensor 42 can be utilized with impedance sensing electrode 38R in a hybrid magnetic and impedance position sensing technique known as ACL described in U.S. Pat. Nos. 7,536,218; 7,756,567; 7,848,787; 7,869,865; and 8,456,182, of which a copy is provided in the priority U.S. Provisional Patent Application 62/841,154 and incorporated herein by reference.

Referring to FIGS. 2D and 2E, the fourth lumen 34 (for example, diametrically opposite of the second lumen 32 in the illustrated embodiment) carries a second puller wire 26. The tubing 19 is made of a suitable non-toxic material that is preferably more flexible than the catheter body 12. One suitable material for the tubing 19 is braided polyurethane, i.e., polyurethane with an embedded mesh of braided stainless steel or the like. The size of each lumen is not critical, but is sufficient to house the lead wires, puller wires, the cable and any other components.

The useful length of the catheter, i.e., that portion that can be inserted into the body excluding the end effector, can vary as desired. Preferably the useful length ranges from about 110 cm to about 120 cm. The length of the intermediate section 14 is a relatively smaller portion of the useful length, and preferably ranges from about 3.5 cm to about 10 cm, more preferably from about 5 cm to about 6.5 cm.

Catheter body 12 can be attached to intermediate section 14 as shown and described in in FIGS. 2A and 2B of U.S. Pat. No. 9,820,664 (of which a copy is provided in the priority US Provisional Patent Application 62/841,154 and incorporated herein by reference). If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which a copy is provided in the priority U.S. Provisional Patent Application 62/841,154 and incorporated herein by reference.

Figure 3:
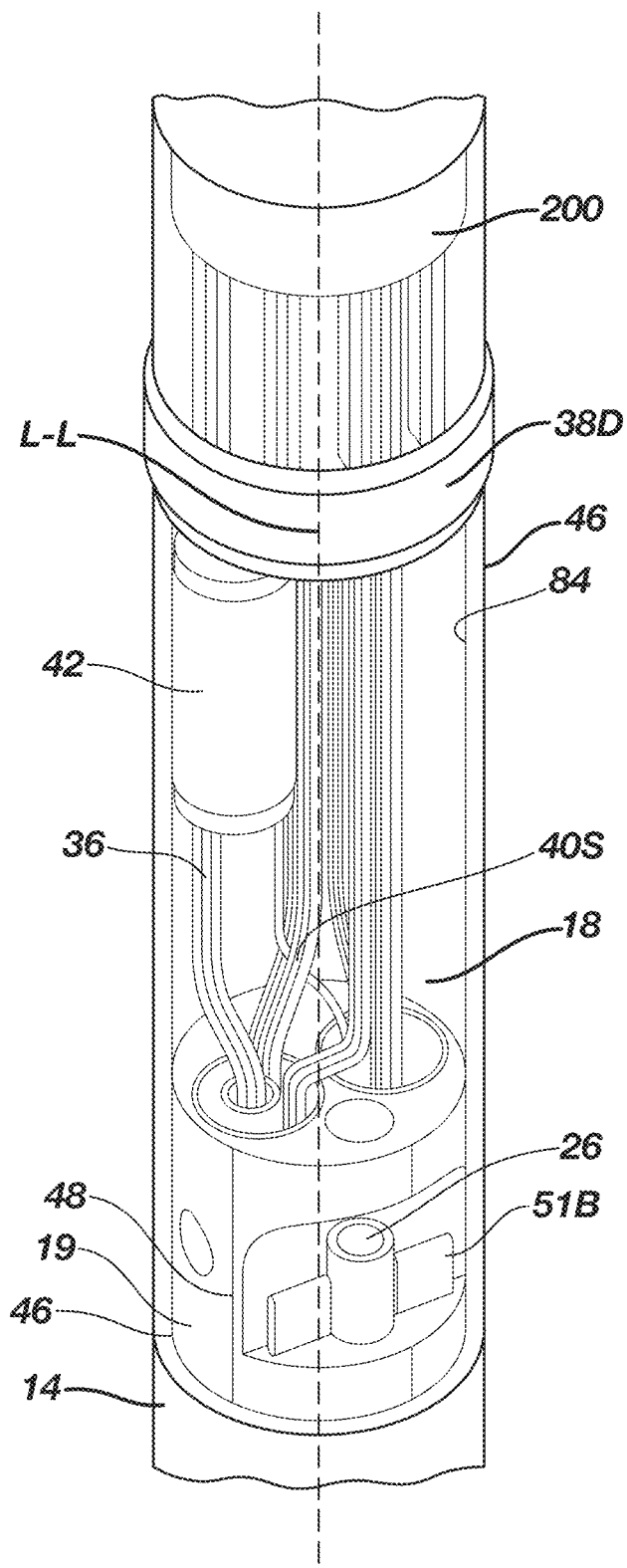
FIG. 3 illustrates in a perspective view of various components disposed in the intermediate section 14 of the catheter of FIG. 1.
Figure 4A:
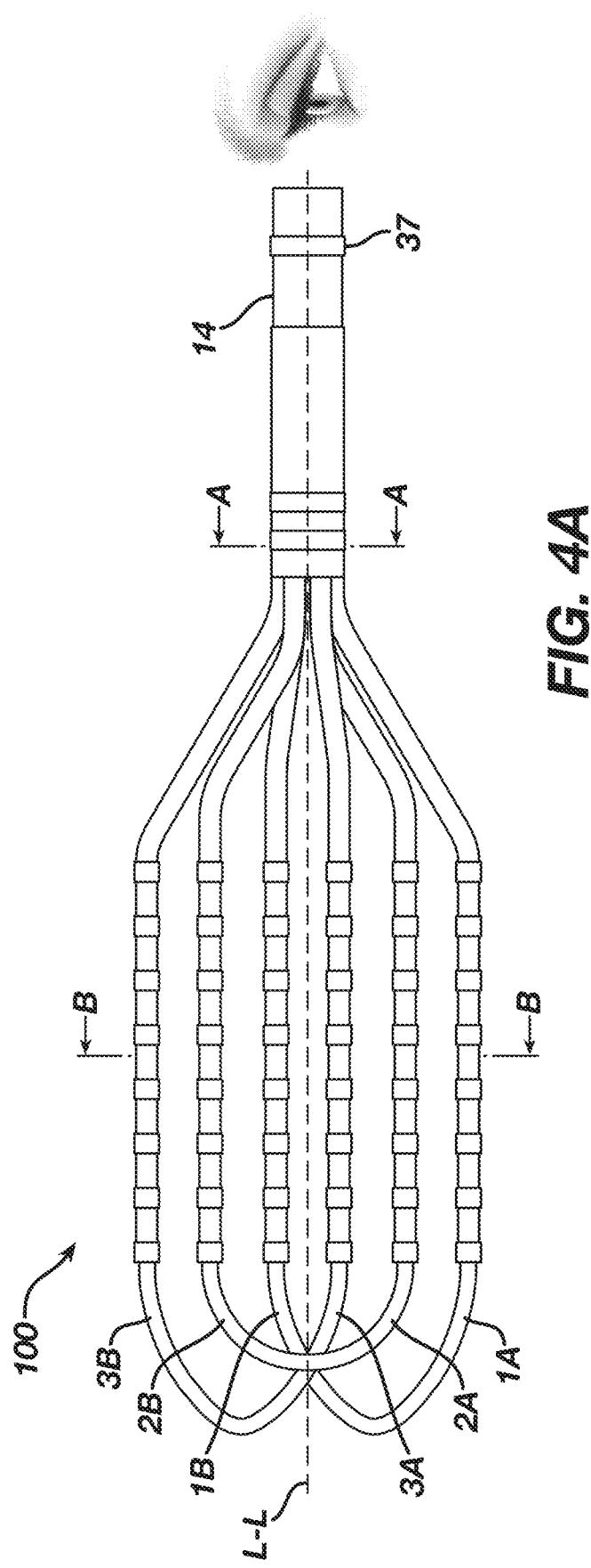
FIGS. 4A, 4B, 4C, 4D and 4E illustrate the spatial configurations of the closed-loop members of the end effector as viewed from a proximal end of the catheter.
Figure 4C:
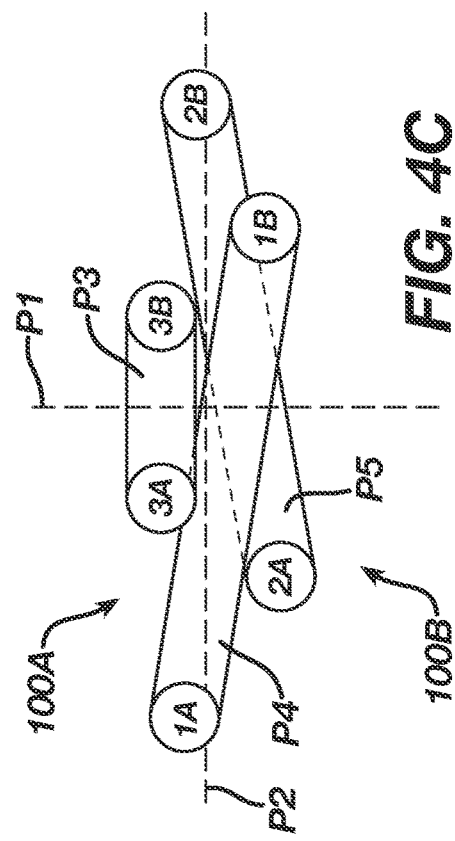
Figure 4E:
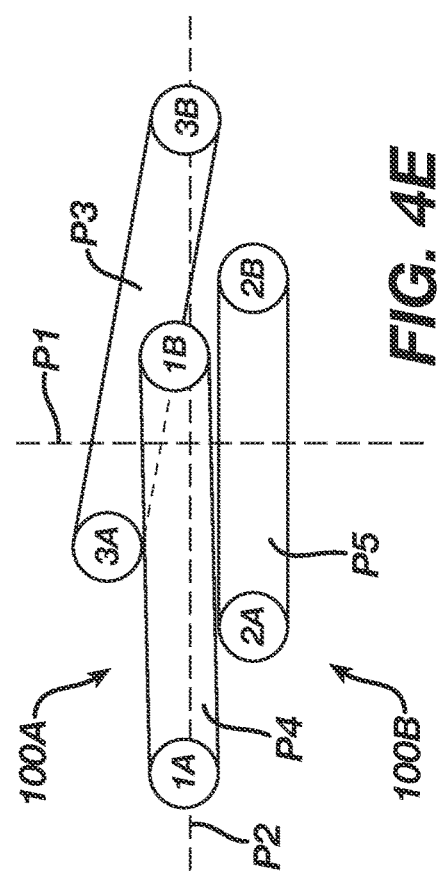
Figure 4B:
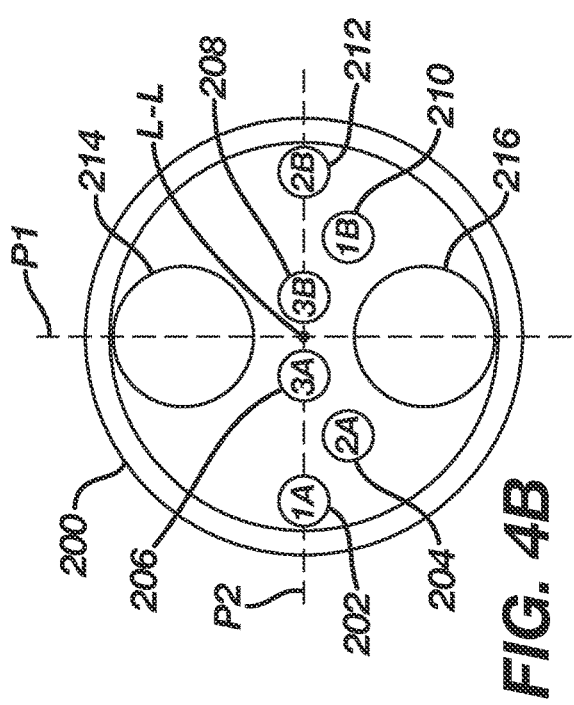

As shown in the perspective view of FIG. 3, the end effector 100 includes a connector tubing 46 mounted on a distal end of the tubing 19 of the intermediate section 14 with insert 200 for connection of spines to the tubular member 14 (FIG. 4B). The connector tubing 46 has a central lumen 48 to house various components. An outer circumferential notch 27 (FIG. 2D) in the distal end of the tubing 19 that receives the inner surface of the proximal end of the connector tubing 46 can be used to attach the connector tubing 46 and the intermediate section 14. The intermediate section 14 and connector tubing 46 are attached by glue or the like.

As also shown in FIG. 3, the connector tubing 46 houses various components, including the electromagnetic position sensor 42, and a distal anchor bar 51A for the puller wire 24 and another anchor bar 51B for wire 26 (only anchor 51B for wire 26 is visible in FIG. 3). Carried on the outer surface of the tubing 19 near the distal end of the intermediate deflection section 14, a distal ring electrode 38D is connected to lead wire formed in the side wall of the tubing 19. The distal end of the lead wire is welded or otherwise attached to the distal ring electrode 38D as known in the art.

Figure 4D:
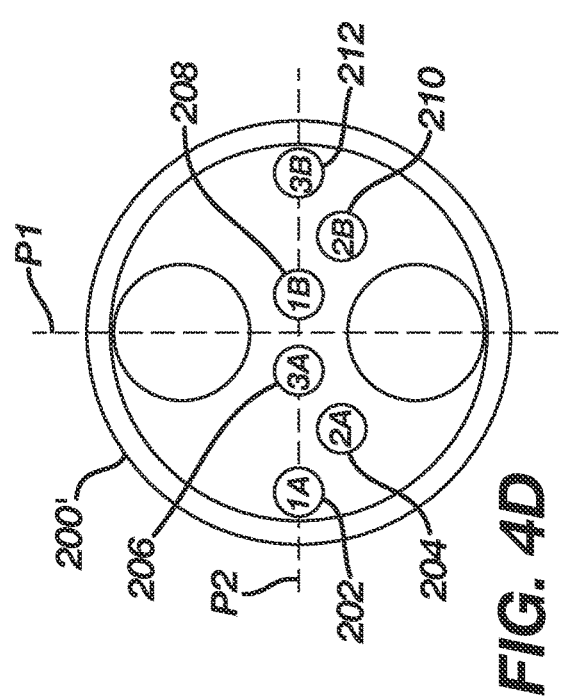

Extending from the distal end of the connector tubing 46 is the end effector 100, shown in FIG. 4A, with a plurality of spines 1A, 1B, 2A, 2B, 3A, 3B all extending in different planes (FIG. 4C and FIG. 4D). Each spine 1A, 1B, 2A, 2B, 3A or 3B may have a length ranging between about 5 and 50 mm, preferably about 10 and 35 mm, and more preferably about 28 mm. The parallel portions of each spine 1A, 1B, 2A, 2B, 3A or 3B (1A, 1B, 2A, 2B, 3A, 3B) may be spaced apart from each other by a distance ranging between about 1 mm and 20 mm, preferably about 2 and 10 mm, and more preferably about 4 mm.

The configuration of the spines 1A, 1B, 2A, 2B, 3A and 3B for loops 1, 2 and 3, in an unconstrained configuration, merits an in-depth discussion in relation to FIGS. 4B, 4C, 4D and 4E. As shown in FIG. 4B, which is a cross-sectional view as viewed from the proximal end of the tubular member 14, there is provided a tubular insert 200 that has its center coinciding with the longitudinal axis L-L. Orthogonal planes P1 and P2 are in alignment with the longitudinal axis to define four quadrants in the insert 200. In the insert 200 shown in FIG. 4B, apertures 202, 204, 206, 208, 210 and 212 are provided for insertion of respective spines 1A, 2A, 3A, 3B, 1B and 2B. It is noted that spines 1A, 3A, 3B and 2B are disposed generally on orthogonal planes P2 whereas spines 2A and 1B are offset from orthogonal planes P1 and P2. Openings 214 and 216 are disposed on orthogonal plane P1 for insertion of puller wires or electrical wires as well as any other components to and from the end effector 100. With this arrangement of apertures 202, 204, 206, 208, 210 and 212, loop members 1, 2 and 3 are therefore arrayed in an unique unconstrained arrangement, shown in the sectional view of FIG. 4C (as viewed from the proximal end), whereby loop 3 defines a plane P3 (demarcated by spines 3A and 3B with connector 3C) that intersects orthogonal plane P1 with loop 1 having a plane P4 (demarcated by spines 1A and 1B with connector 3C) that intersects both orthogonal planes P1 and P2 and loop 2 having a plane P5 (demarcated by spines 2A and 2B and connector 2C) that intersects both orthogonal planes P1 and P2.

In an alternate embodiment of insert 200, shown in FIG. 4D as insert 200', apertures 202, 204, 206, 208, 210 and 212 are arranged differently than the arrangement of apertures in FIG. 4B. Specifically, spine 1A and spine 1B of loop 1 are now received into apertures 202 and 208 so that the apertures 202 and 208 (as well as spines 1A and 1B) are arranged to be on the same plane as orthogonal plane P2 (instead of being offset as in FIG. 4B). Spines 3A and 3B are received in apertures 206 and 212 which are on orthogonal plane P2. Spines 2A and 2B are received in apertures 204 and 210 which are offset with respect to orthogonal plane P2. Due to the arrangement of spines in the apertures of FIG. 4D, loops 1, 2 and 3 are therefore arranged in the sectional view (as viewed from the proximal end) of FIG. 4D. In FIG. 4D, the loops 1, 2 and 3 are unconstrained (shown in plan view of FIG. 4A) or released from a delivery sheath. In the unconstrained configuration, the third loop 3 defines a plane P3 (extending between spines 3A and 3B) that intersects both orthogonal planes P1 and P2; first loop 1 defines a plane P4 (extending between spines 1A and 1B) that intersects both orthogonal planes P1 and P2; and second loop 2 defines a fifth plane P5 (extending between spines 2A and 2B) that intersects only orthogonal plane P1. To summarize, an insert 200 (or 200') is provided near the distal portion 14D that has first and second openings 214 and 216 intersecting the first orthogonal plane P1 and extending along the longitudinal axis L-L such that each of the openings 214 and 216 is configured to receive a puller wire (24 or 26). The insert 200 (or 200') includes six apertures 202, 204, 206, 208, 210, 212 disposed between the first and second openings 214, 216 with four apertures (206, 208) intersecting the second orthogonal plane P2, each of the apertures configured to receive a spine member that collectively define an end effector 100 coupled to the distal portion 14D. The end effector 100 has three closed-loop members with each loop having two spines so that six spine members of the three closed-loop members are disposed in the respective six apertures of the distal portion of the catheter.

It is noted that the loops 1, 2 and 3 provided herein and their planar orientations enables location sensing of the loops themselves because each loop acts as a single-axis magnetic coil. With three loops arrayed in three spatial configurations, the loops can be used as a three-axis magnetic sensor to sense the magnetic field that is generated around the patient using the Carto3 mapping system. Briefly, each pair of spines A and B is conductive and is connected via connector C, terminates at different planar orientations (P3, P4, P5 in FIG. 4C or FIG. 4E), and encloses a region defined by the loop (1, 2 or 3). It will be understood that the specific loop acts as a coil having a single turn. Thus, when the region enclosed by the single turn coil (one loop) is traversed by alternating magnetic fields from radiators disposed around a subject, Faraday's law of induction provides that an induced voltage is developed across the different second terminations of the pair, and that the voltage depends on the area of the region enclosed, the intensity of the magnetic fields at the region, and the orientation of the region with respect to the magnetic fields.

Single axis sensors (SAS) having a coil with multiple turns are known in the art, and providing they are positioned in alternating magnetic fields that have been spatially mapped, it will be understood that the voltage developed across the SAS coil can be used to find the position and orientation of the SAS coil in the magnetic field. FIG. 6 of US20180344202 (of which a copy is provided in the priority U.S. Provisional Patent Application 62/841,154 and incorporated herein by reference) describes an algorithm for finding the position and orientation of an SAS in a mapped magnetic field, and those of skill in the art will be able to use the description of the algorithm, mutatis mutandis, to find the position and orientation of a single turn coil, such as a specific single turn coil defined by a pair of spines (or loop). For n conductors where n is an integer equal to or greater than 2, there are (n|2) different possible pairs of conductors forming single turn coils generating (n|2) respective voltages. Thus, for the 6 conductors (in their respective splines) considered here, there are at least 3 possible different single turn coils. The voltage across each single turn coil gives the position and orientation of the coil, known or can be estimated. From the geometric relationships, and from the voltages developed by the various single turn coils, a processor in the CARTO3 system can estimate the position and orientation end effector 100. Each opposing pair of conductive spines in general forms a planar ellipse for a total of three planar ellipses. By virtue of the configuration of the spines and loops being known (as provided herein), the orientation of the three loops 1, 2, and 3 with respect to each other will be known and therefore this orientation can be used to calculate an orientation of the overall shape of the end effector 100. Details of a single conductive member such as the loop functioning as single axis magnetic sensing coil in combination with other loops are provided in U.S. patent application Ser. No. 15/971,966 published as US20180344202, the entirety of which a copy is provided in the priority U.S. Provisional Patent Application 62/841,154 and incorporated herein by reference.

Figure 5A:
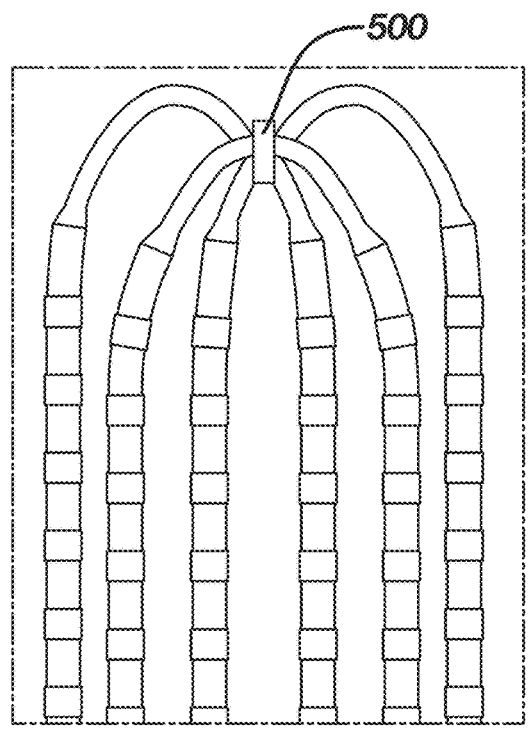
Figure 5B:
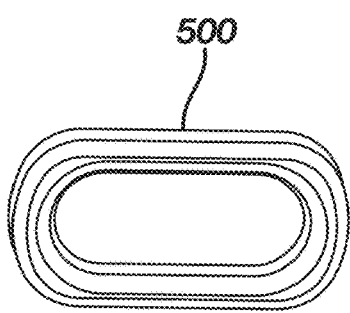
Figure 5C:
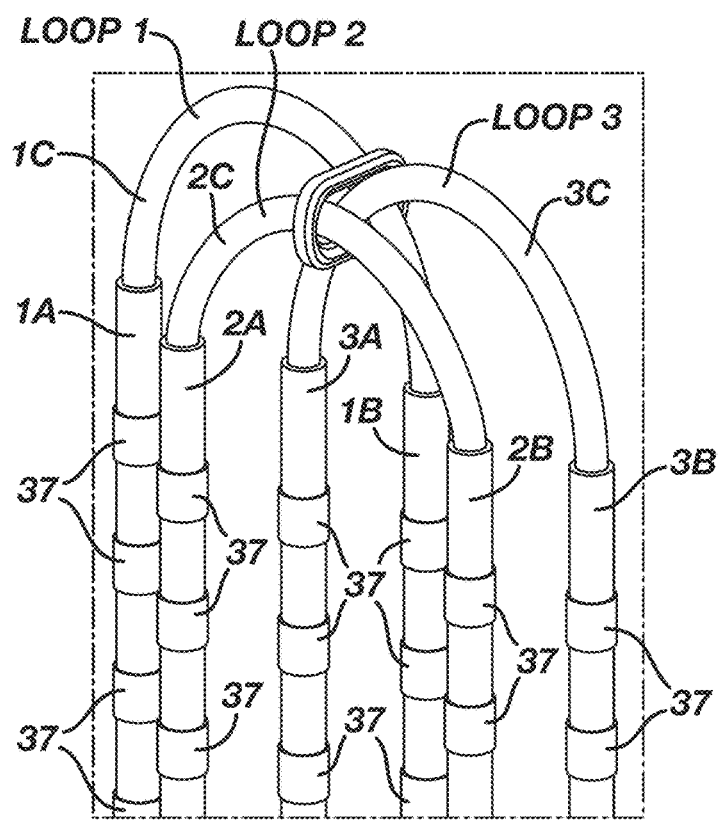
Figure 5E:
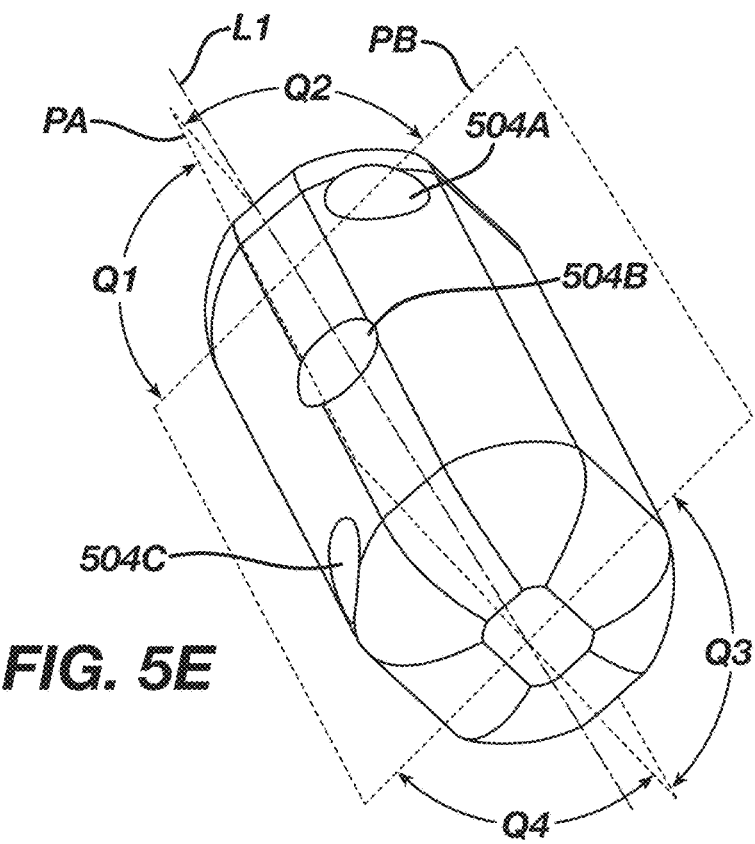
Figure 5F:
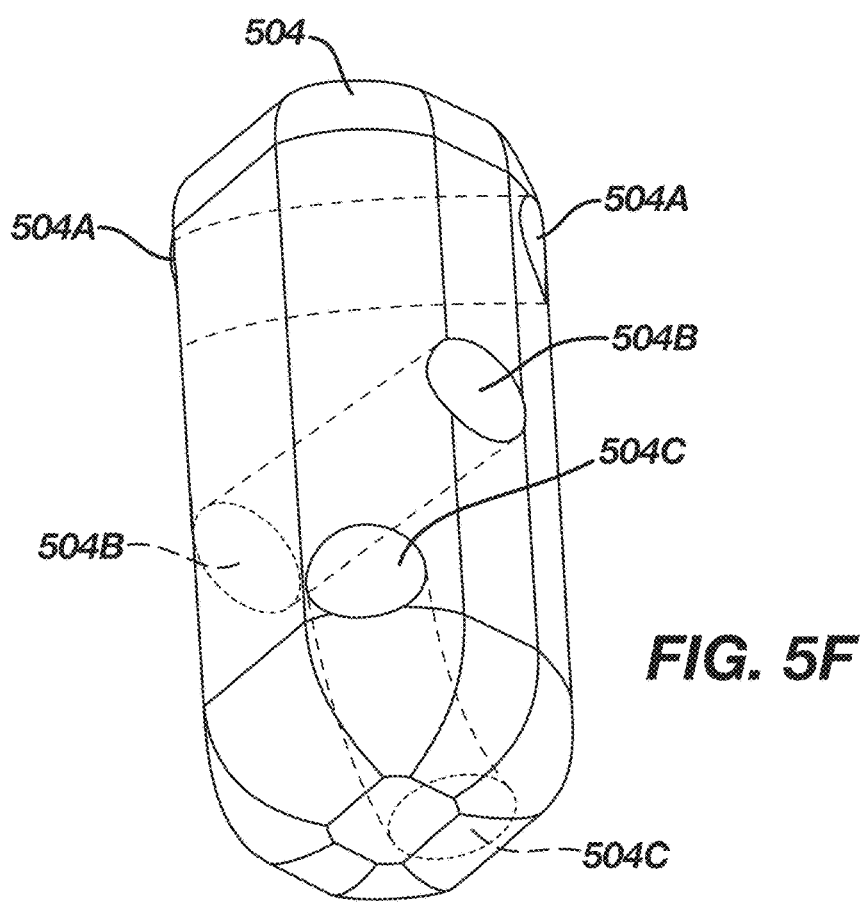

The unique planar configurations of end effector 100 in FIGS. 4A-4D presented some challenges in maintaining a generally constant spacing between the spines when the end effector 100 is unconstrained. In particular, where the connectors 1C, 2C and 3C converge, it is beneficial to connect the loops together with a separate member such as, for example, a clip 500, shown here coupling to connectors 1C, 2C, and 3C together in a single connection point in FIG. 5A. Clip 500 can be an elongated curvilinear member shown in a perspective view of FIG. 5B and as assembled with end effector 100. Alternatively, clip 500 can be in the form of a circular ring. In circumstances where the loops 1, 2 and 3 are in a spatially fixed arrangement such as that shown in FIG. 5D, coupling block 504 can be utilized to ensure that the connectors 1C, 2C and 3C are arranged in a fixed spatial configuration whereby the first connector 1C extends through first passage 504A, second connector extends through passage 504B and third connector 3C through third passage 504C. Passages 504A, 504B and 504C are shown in an enlarged perspective view of coupling block 504 in FIG. 5E. Coupling block 504 includes a longitudinal axis L1 that extends through the center of block 504. A plane PA (similar to orthogonal plane P1) is orientated so that plane PA extends along the longitudinal axis L1 (similar to longitudinal axis L-L) and orthogonal plane PA bisects second passage 504B. Another plane PB extending along axis L1 (similar to orthogonal plane P2) and orthogonal to plane PB is defined so that four quadrants Q1, Q2, Q3 and Q4 can be defined as follow: quadrant Q1 is the upper left sector contiguous to or left of plane PB and contiguous to or above plane PA, quadrant Q2 is the upper right sector contiguous to or to the right of plane PA and contiguous or above plane PB; quadrant Q3 is the lower right sector between the right of plane PA and contiguous to or below plane PB; and quadrant Q4 is the sector to the left of plane PA and contiguous to or below plane PB. Passage 504A extends through coupling block 504 from quadrant Q2 to quadrant Q4; passage 504B extends along plane PA through plane PB such that passage 504B extends through all quadrants; and passage 504C extends from quadrant Q1 to quadrant Q3. It is noted that clip 500, ring 502 or coupling block 504 can be formed from a biocompatible material such as, for example, nitinol or a polymer. Biologics such as for example, heparin or suitable blood thinner can be added to the nitinol or polymer for elution while in the organ or artery of a biological subject.

Figure 6A:
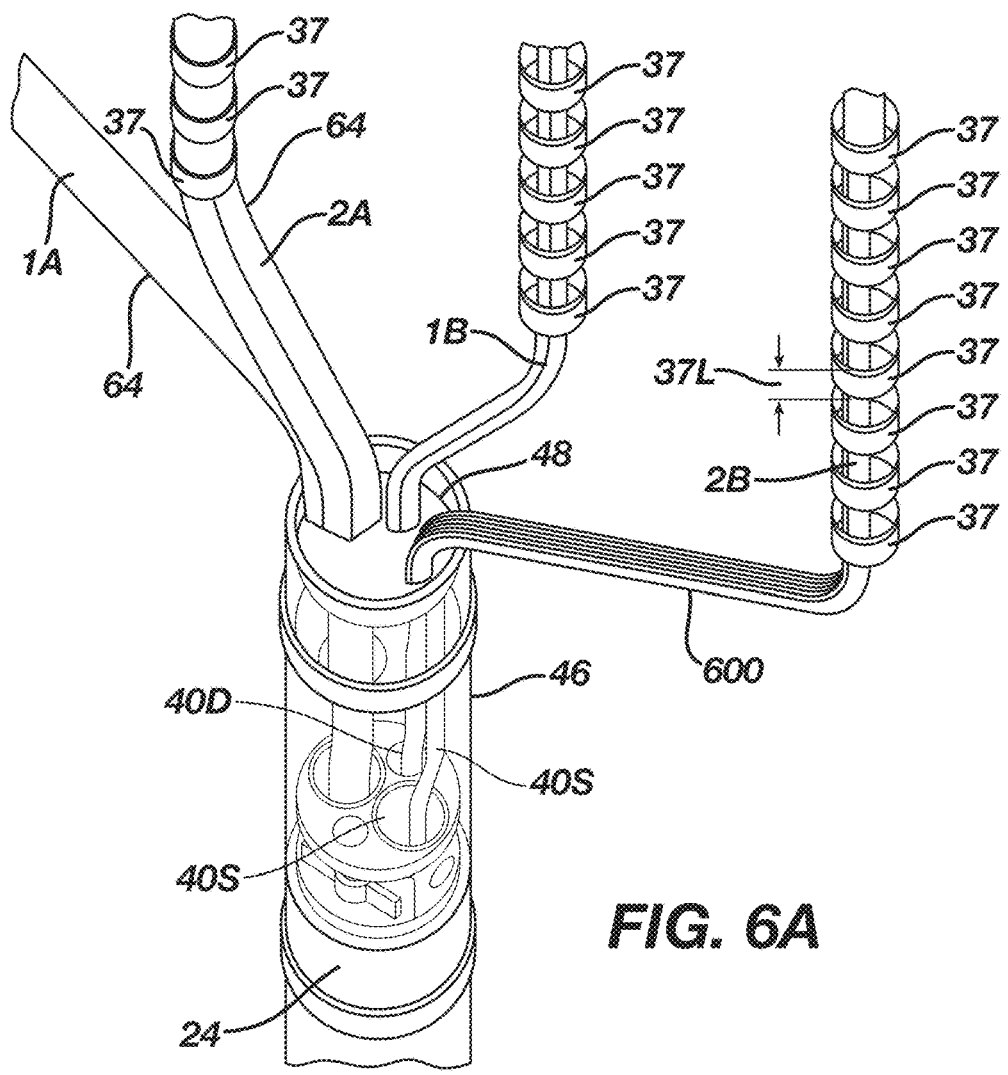
FIGS. 6A and 6B illustrate close up perspective view of the structural backbone of each spine that extends out of an insert member located in the distal portion of member 14 and various wirings and covering for the spines as well as electrodes mounted on each spine.
Figure 6B:
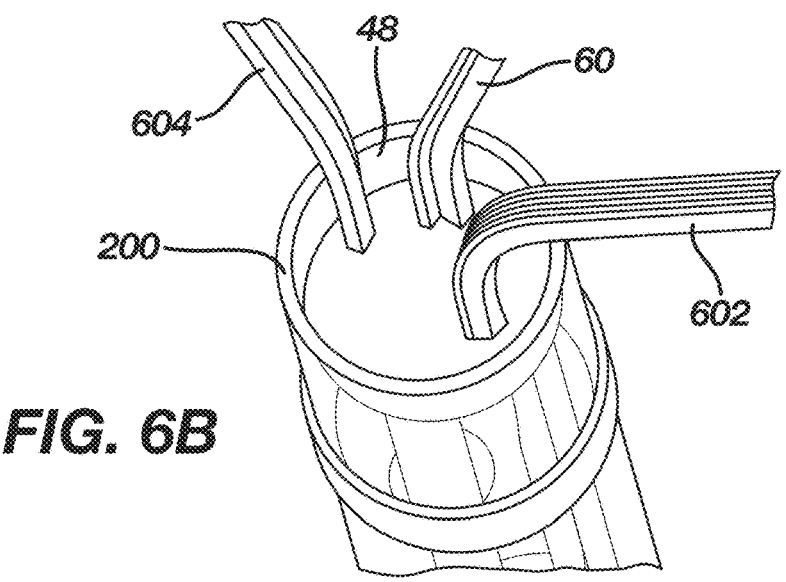
Figure 6C:
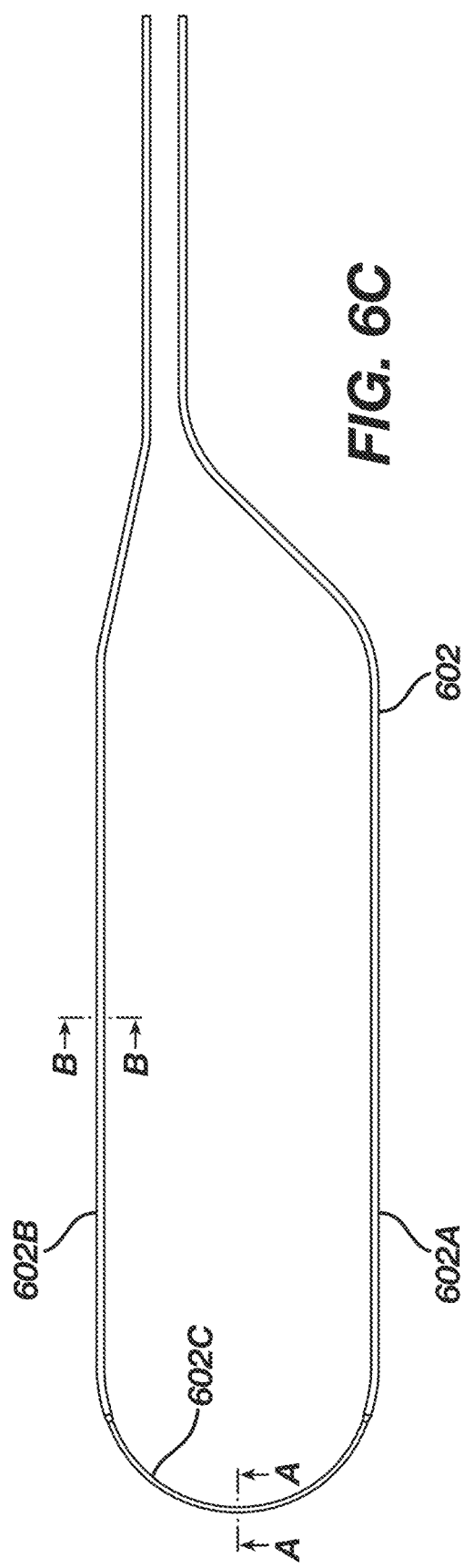
FIGS. 6C, 6D and 6E illustrate a non-symmetrical structural backbone of the spines of first and third loop members as well as the necessary cross-sections.
Figure 6E:
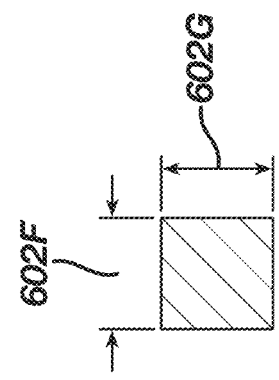
Figure 6D:
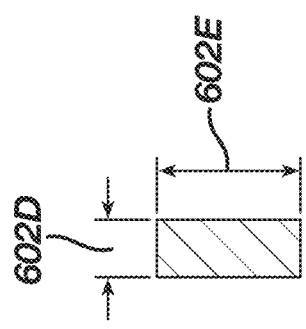

As shown in FIGS. 6A and 6B, four spines 1A, 1B, 2A and 2B are shown with the cover on spine 1B and 2B removed so that structural member 600 for loop 1 can be seen. That is, each loop with spine (1A, 1B; 1C; 2A; 2B; 2C; 3A; 3B; 3C) has an elongated shape memory member 600 extending through the length of the spine to and from insert member 200. While the preferred embodiment has all three segments of a loop (e.g., loop 1 with segment 1A, segment 1B, and segment 1C) formed from a single unitary material, it is within the scope of this invention that the three segments can be discrete components affixed to each other. A proximal portion of each loop structural member 602 or 604 extends into a distal end portion of the connector tubing 46 and is anchored in the lumen 48 into insert 200 (FIGS. 4B and 4D). To ensure that the loops 1, 2, 3 can be compressed into a very small shape for delivery into a vessel, we have devised the first loop 1 and third loop 3 to have a structural member 602 in the asymmetric configuration shown in FIG. 6C while structural member 604 for the second loop 2 has the symmetric configuration of FIG. 6F. Structural member 602 has a first portion 602A (forming first spine 1A or third spine 3A), second portion 602B (forming second spine 1B or third spine 3B) with a connector portion 602C (forming connector 1C or connector 3C) that connects to both portions 604A and 604B. Structural member 604 (FIG. 6F) has a first portion 604A (forming spine 2A) with a second portion 604B (forming spine 2B) with a connector portion 604C (forming connector 2C) that connects both portions 604A and 604B. As shown in FIG. 6D, the connector portion 604C has a rectangular cross-section with an area of approximately 0.41 mm squared while the first and second portions 604A and 604B has a square shaped cross-section of approximately 0.41 mm squared. Given that the nitinol wire is cold-formed, the cross-sectional area does not change significantly. Consequently, the area moments of inertia of the nitinol (along the X and Y axis) are equal at the square nitinol section and the bending-stiffness ratio is about 4:1 at the cold formed portion of the nitinol radius. Hence, it takes about four times less force to bend the nitinol in one plane verses the other at the loop radius. The nitinol is compression shaped from a wire to arrive at the rectangular or square shaped cross-sections. The preferred compressed nitinol radius dimensions are approximately 0.127 mm (~0.005 inches) in thickness by 0.33 mm (~0.013 inches) in width. The range of thickness is from 0.101 mm to about 0.152 mm (~0.004 inches to ~0.006 inches) in thickness and the range of width is from about 0.28 mm to about 0.46 mm (~0.011 inches to ~0.019 inches) in width. The preferred nitinol wire form to create the loop is about 0.21 mm (~0.008 inches by 0.008 inches) square in cross-section. The range of nitinol wire that can be utilized to form the loops are from about 0.18 mm to about 0.25 mm (~0.007 inches to 0.010 inches) square. Round wire in the range for 0.18 mm to about 0.25 mm (0.007 inches-0.010 inches) in diameter could also be used to form the loops.

Each spine 1A, 1B, 2A, 2B, 3A or 3B1A, 1B, 2A, 2B, 3A or 3B also has a nonconductive covering 64 that covers the shape memory member 600 and each spine 1A, 1B, 2A, 2B, 3A or 3B carries a plurality of ring electrode 37 that can be from 48-124 electrodes in total. Accordingly, the end effector 100 carries a plurality of electrodes from 48 to 64, preferably between about 48 and 100 electrodes, and more preferably about 48 electrodes. The surface area of the end effector 100 may range between about 10 $cm^2$ to 50 $cm^2$, preferably between about 15 $cm^2$ and 25 $cm^2$, and more preferably about 22.4 $cm^2$. In some embodiments, the electrode density is about 5 electrodes per square centimeter and dimensions of about 0.7 mm by 0.7 mm.

With shape memory in its spines 1A, 1B, 2A, 2B, 3A, 3B, the end effector 100 can assume at least two configurations: a deployed configuration with the spines 1A, 1B, 2A, 2B, 3A, 3B splayed out in one of the configurations shown in FIGS. 4B, 4C, 4D and 4E, and a collapsed configuration where the spines can be bundled generally along the longitudinal axis L-L.

The support member 600 is made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium but may comprise from about 54% to about 57% nickel with the balance being titanium. A nickel/titanium alloy is nitinol, which has excellent shape memory, together with ductility, strength, corrosion resistance, electrical resistivity and temperature stability. The non-conductive covering 64 can be made of any suitable material and is preferably made of a biocompatible plastic such as polyurethane or PEBAX. If desired, the support member 600 can be eliminated and the distal end of the non-conductive covering 64 can be preformed to have the desired curvature or configuration.

Each shape-memory support member 600 extending through its respective nonconductive covering 64 has a proximal end that is received and anchored in the distal end of the connector tubing 46 by a suitable coupler (e.g., FIGS. 5A-5F). Lead wires 40S for the spine electrodes 37 extend through a protective distal polytube 68D. They diverge at the distal end of the connector tubing 46, and extend alongside their respective shape memory member 600, into their respective nonconductive covering 64 of their respective spines 1A, 1B, 2A, 2B, 3A, 3B. Each lead wire 40S is connected to its respective spine ring electrode 37 via a respective opening (not shown) formed in the side wall of the covering 64 through which a distal end of the lead wire reaches outside of the covering 64 and is welded or otherwise attached to its spine ring electrode 37, as known in the art.

At the junction of end effector 100 and the connector tubing 46, the non-conductive covering 64 of each spine 1A, 1B, 2A, 2B, 3A or 3B is attached and sealed at its proximal end to the tubing 46 by the polyurethane adhesive or the like. If desired, the proximal ends of the support members 600 can extend further proximally into the connector tubing 46. Polyurethane or the like is also applied to the distal end of each spine to seal the distal end and provide an atraumatic dome.

As mentioned above, the end effector 100 can assume at least two configurations: a deployed, expanded configuration (FIG. 5A) and a collapsed configuration (not shown). With the end effector 100 in the deployed, expanded configuration, the proximal portion 17P of each spine splays out and extends generally in various planes as described in relation to FIGS. 4C and 4E, with the outer spines 1A and 3B spreading outwardly at a greater angle away from the longitudinal axis L-L of the catheter and the inner spines 3A and 1B spreading outwardly at a lesser angle away from the longitudinal axis L-L. With the end effector 100 in the collapsed configuration, spines are bundled into a generally cylindrical form for delivery through the patient's anatomy via a suitable sheath.

The proximal ends of the lead wires 40S and 40D are electrically connected to a suitable connector (not shown) in the distal end of the control handle 16, which is connected to an input device to sense electrical signals generated in the tissues (e.g., electrocardiograms) allowing the end-effector to be a mapping catheter for mapping electrocardiogram signals. Alternatively, the electrodes 37 can be connected to source of ablation energy, e.g., RF energy to perform ablation of tissues, as is known in the art.

In the depicted embodiment (FIG. 3), the lead wires 40S extending through the central lumen 18 of the catheter body 12 and the lumen in the deflection section 14 may be enclosed within a protective sheath to prevent contact with other components in the catheter. The protective sheath can be made of any suitable material, preferably polyimide. As would be recognized by one skilled in the art, the protective sheath can be eliminated if desired.

The ring electrodes 37 and 38D, 38P and 38R can be made of any suitable solid conductive material, such as platinum or gold, preferably a combination of platinum and iridium, and mounted onto the non-conductive cover 64 and the connector tubing 46 with glue or the like. Alternatively, the ring electrodes can be formed by coating the non-conductive cover 64 and connector tubing 46 with an electrically conducting material, like platinum, gold and/or iridium. The coating can be applied using sputtering, ion beam deposition or an equivalent technique.

Figure 7A:
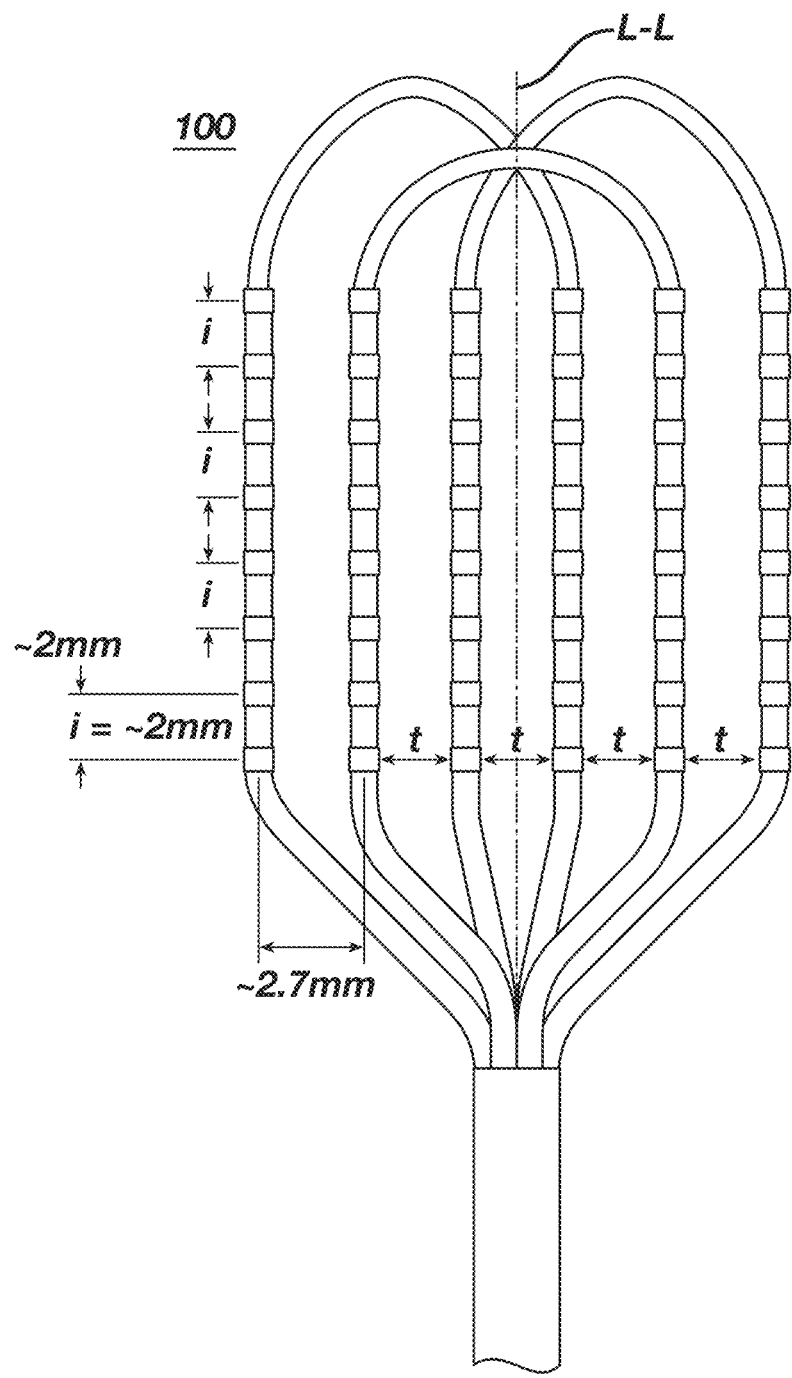
FIGS. 7A, 7B, 7C and 7D illustrate various "grid-like" configurations and dimensions of the electrodes on each spine.
Figure 7B:
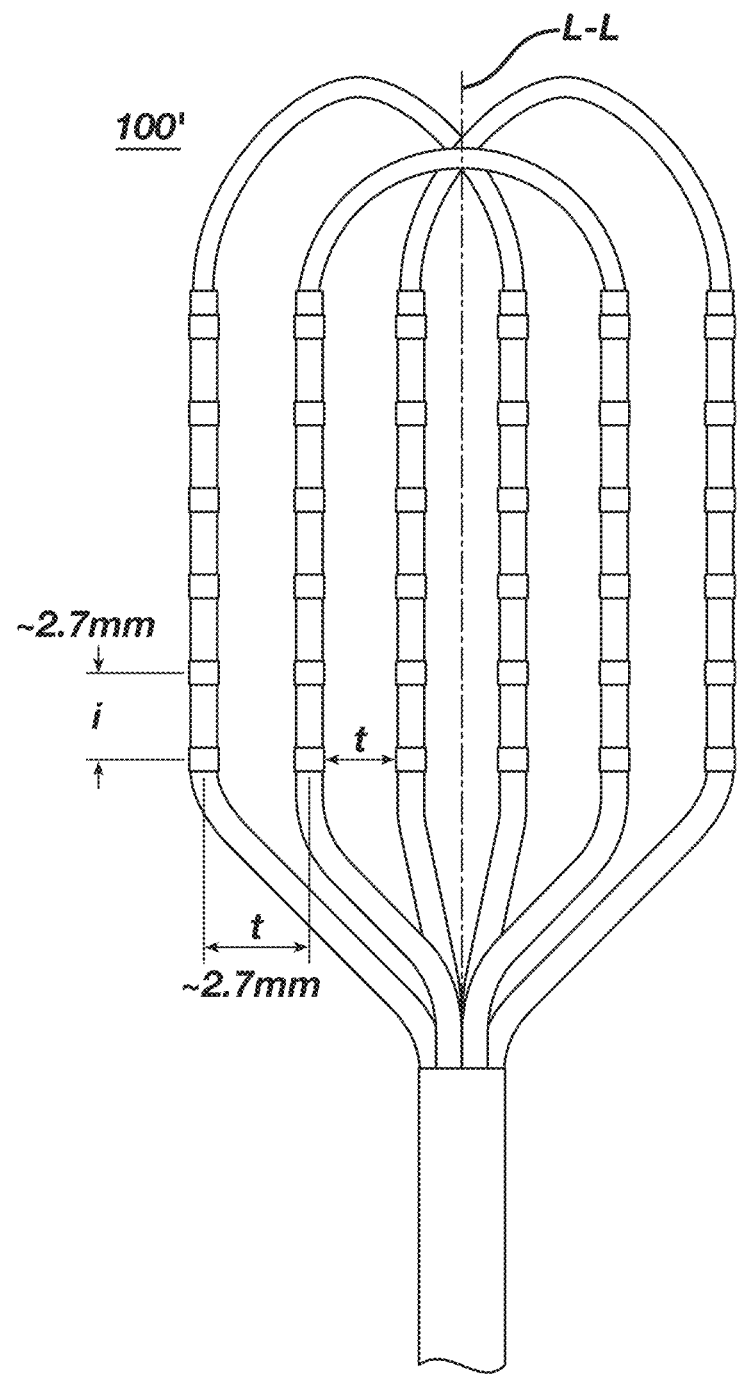
Figure 7C:
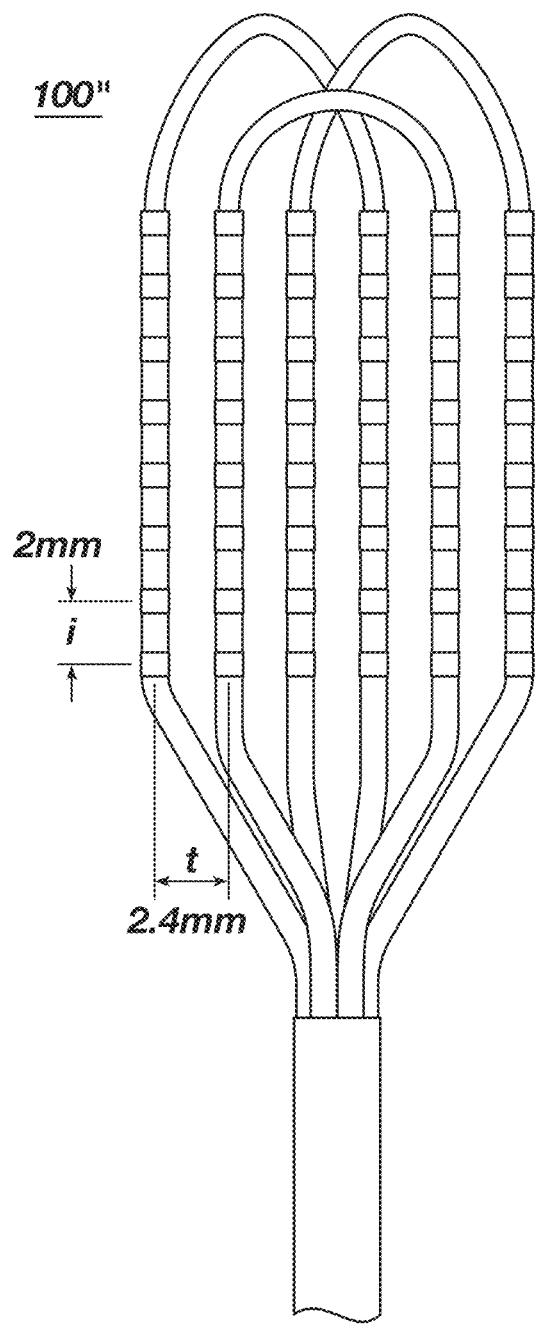
Figure 7D:
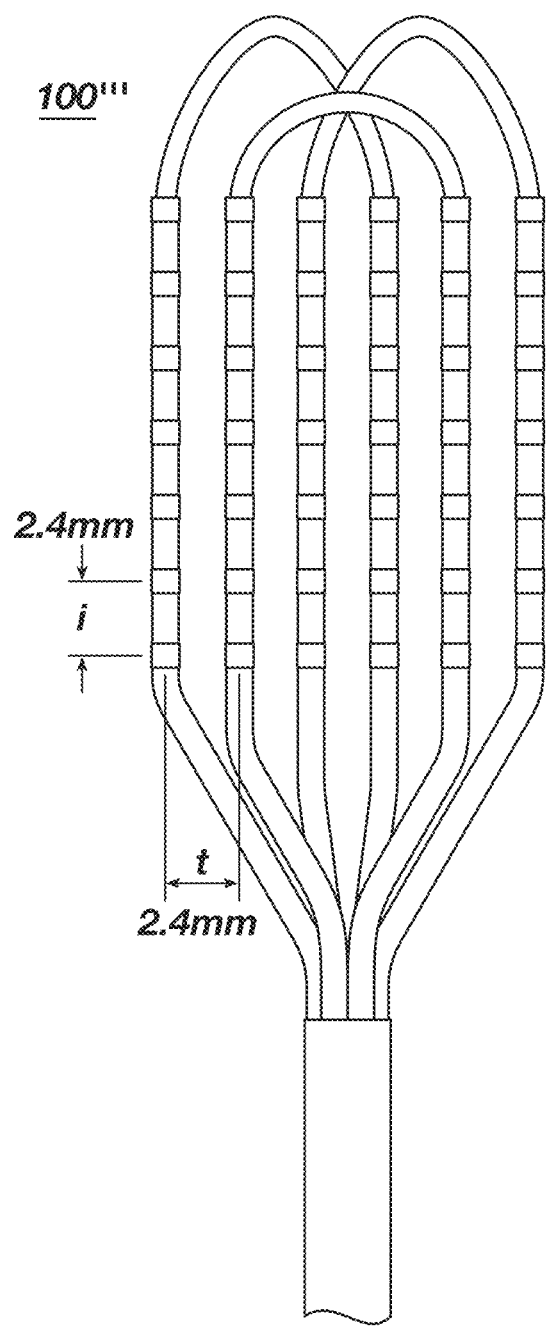

The ring electrodes 37 on the spines 1A, 1B, 2A, 2B, 3A, 3B can be approximately evenly spaced along each spine. They may form any desirable pattern, for example, a "rectangular grid" pattern (100 in FIG. 7A or 100" in FIG. 7C) or a "square grid" pattern (100' in FIG. 7B and 100'" in FIG. 7D). In the rectangular grid of FIG. 7A, the electrodes 37 are spaced along the longitudinal axis L-L at intervals "i" of approximately 2 mm and spaced apart transverse to the longitudinal axis L-L at intervals "t" of approximately 2.7 mm while in the embodiment of FIG. 7C, the interval "i" is approximately 2 mm and the transverse interval "t" is approximately 2.4 mm. In the square grid of FIG. 7B, the interval "i" is approximately 2.7 mm and the interval "t" is approximately 2.4 mm while in FIG. 7D, the interval "i" is equal to interval "t" of about 2.4 mm.

In another embodiment, each spine may have "paired" electrodes comprising of pairs of closely-spaced ring electrodes. As used herein, the term "ring electrode pair" refers to a pair of ring electrodes that are arranged closer to each other than they are to the other adjacent ring electrodes. In some embodiments, the distance between two electrodes of an electrode pair is less than about 3 mm, more preferably less than about 2 mm, still more preferably from about 0.5 mm to about 1.5 mm. The number of electrode pairs can vary as desired, and preferably ranges from 3 to 36 pairs, more preferably 24 pairs.

The end effector 100 may carry, for example, 24 (4 pairs of electrodes×6 spines in FIG. 1, 2A, 2B, 2C or 2D) with a space of approximately 1 mm to approximately 2 mm between the two electrodes of each pair. Preferably each ring electrode 37 is relatively short, having a length 37L ranging from about 0.4 mm to about 0.75 mm. Regardless of the size and number of the ring electrodes 37, the electrode pairs are preferably approximately evenly spaced along the end effector 100. The closely-spaced electrode pairs allow for more accurate detection of near field pulmonary vein potential versus far field atrial signals, which is very important when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

An electromagnetic position sensor 42 is housed in the lumen of the nonconductive covering 46 (FIG. 3). A sensor cable 36 extends from a proximal end of the position sensor 42, and through the central lumen 18 of the catheter body 12. The cable 36 is attached to a PC board in the control handle 16, as known in the art.

The puller wires 24 and 26 (whether as two separate tensile members or parts of a single tensile member) are provided for bi-directional deflection of the intermediate section 14. The puller wires 24 (FIG. 6A) and 26 (FIG. 3) are actuated by mechanisms in the control handle 16 that are responsive to a thumb control knob or a deflection control knob 11. Suitable control handles are disclosed in U.S. Pat. Nos. 6,123,699; 6,171,277; 6,183,435; 6,183,463; 6,198,974; 6,210,407 and 6,267,746, the entire disclosures of which a copy is provided in the priority U.S. Provisional Patent Application 62/841,154 and incorporated herein by reference.

Details of the construction of puller wires including anchor via T-bars at the intermediate section 14, as known in the art and described in, for example, U.S. Pat. Nos. 8,603,069 and 9,820,664, the entire content of which is incorporated herein by reference. In any case, the puller wires 24 and 26 are made of any suitable metal, such as stainless steel or Nitinol, and each is preferably coated with TEFLON or the like. The coating imparts lubricity to the puller wires. The puller wires preferably have a diameter ranging from about 0.006 to about 0.010 inch.

Figure 8:
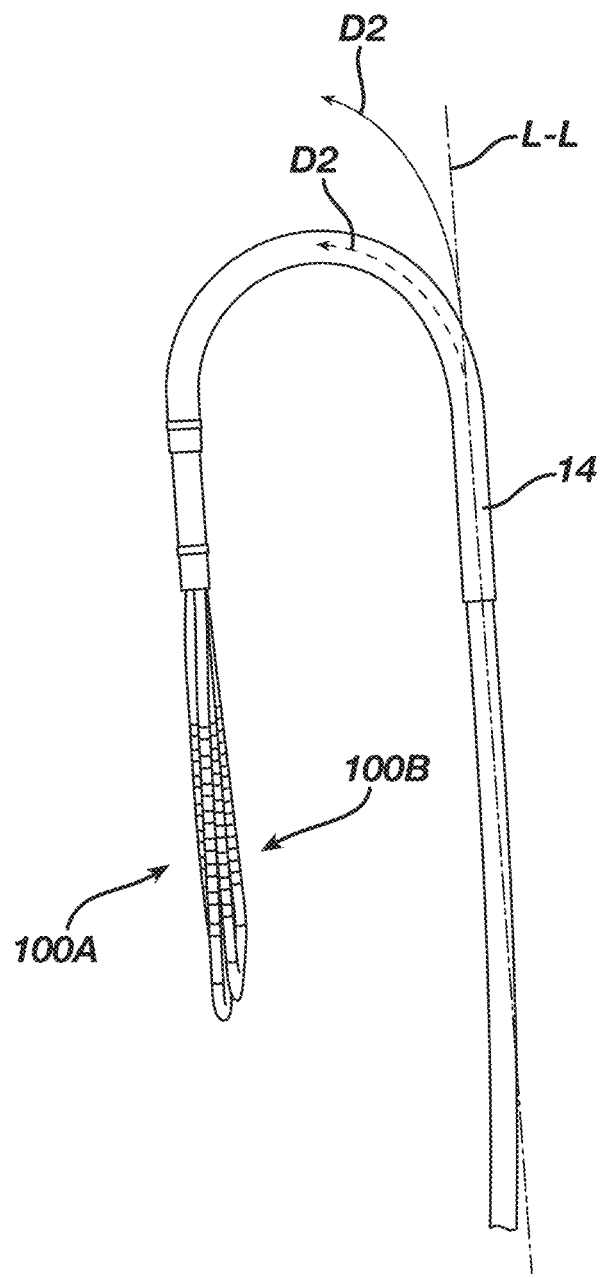
FIG. 8 illustrates the deflection capability of the intermediate section 14 with a puller wire.

In use, a suitable guiding sheath (not shown) is inserted into the patient with its distal end positioned at or near a desired tissue location for diagnostics such as mapping and/or treatment such as ablation. An example of a suitable guiding sheath for use in connection with the present invention is the Preface Braided Guiding Sheath, commercially available from Biosense Webster, Inc. (Irvine, Calif.). The catheter 10 is passed through the guiding sheath and advanced therethrough to the desired tissue location. In particular, the spines 1A, 1B, 2A, 2B, 3A, 3B of the end effector 100 are collapsed and straightened and fed into the proximal end of the guiding sheath. After the end effector 100 has reached the desired tissue location, the guiding sheath is pulled proximally, exposing at least the spines 1A, 1B, 2A, 2B, 3A, 3B, if not also the deflectable intermediate section 14, as needed. Outside of the guiding sheath, the spines 1A, 1B, 2A, 2B, 3A, 3B assume the deployed configuration where each spine splays out and extends generally in the multi-planar configurations of FIGS. 4C and 4D. The end effector 100 has a first side 100A and a second side 100S (FIGS. 4C, 4D and 8). This allows the user to place first side 100A (or 100B) against the tissue surface, with at least the intermediate section 14 (if not also a distal portion of the catheter body 12) generally perpendicular to the tissue surface, and actuates the control handle to deflect the intermediate deflection section 14 to arrive at various deflections or radii of curvature (e.g., arrows D1 and D2 in FIG. 8) such that the second side 100S deflects back toward the catheter, which may allow dragging of the second side 100S of the end effector 100 including loops 1, 2 and 3 across the tissue surface as the section 14 is deflecting.

In use, the spine electrodes 37 are in contact with the tissue surface generally maintaining a consistent separation spacing from each other within the distal electrode matrix as the spines are dragged across the tissue surface for high density electrode sensing and uniform and predictable mapping. In accordance with a feature of the invention, the end effector 100 has an "n×m" electrode layout or arrangement, for example, six spines, with eight electrodes on each spine, for a total of 48 closely-spaced spine electrodes for mapping.

In some embodiments, the distal and proximal ring electrodes 38D and 38P serve as reference electrodes for visualization of the catheter on a 3-D mapping system, such as CARTO. 3 SYSTEM available from Biosense Webster, Inc., which automatically locates the electromagnetic sensor 42, processes reference location values from electrodes 38D and 38P, which are at a constant location from the electromagnetic sensor 42 and determines the location of the spine electrodes 37 and visualizes the remainder of the electrode end effector 100.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of skill in the art, the drawings are not necessarily to scale. Also, different features of different embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter for electrophysiology applications, the catheter includes:
   a tubular member extending along a longitudinal axis from a proximal portion to a distal portion, the distal portion having a cross-section disposed about the longitudinal axis, the cross-section intersecting first and second orthogonal planes that extend along the longitudinal axis, the cross-section of the distal portion includes:
      first and second openings intersecting the first orthogonal plane and extending along the longitudinal axis, each of the openings configured to receive a puller wire;
      six apertures disposed between the first and second openings with four apertures intersecting the second orthogonal plane, each of the apertures configured to receive a spine member; and
   an end effector coupled to the distal portion, the end effector including first, second and third closed-loop members, the end effector having an unrestrained configuration in which:
      the first closed-loop member includes a first spine connected to a second spine with a first loop connector portion to define a first generally planar surface between the first spine, first loop connector portion and second spine such that the first generally planar surface intersects the first and second orthogonal planes,
      the second closed-loop member includes a third spine connected to a fourth spine with a second loop connector portion to define a second generally planar surface between the third spine, second loop connector portion and fourth spine such that the second generally planar surface intersects the first and second orthogonal planes, and
      the third closed-loop member includes a fifth spine connected to a sixth spine with a third loop connector portion to define a third generally planar surface that intersects only one of the first and second orthogonal planes.

2. The catheter of claim 1, in which each spine of the first, second, and third closed-loop members comprises: an elongated member having a rectangular cross-section and providing a structural support for the respective spine.

3. The catheter of claim 2, in which the elongated member comprises a shape memory material.

4. The catheter of claim 3, in which the shape memory material comprises nitinol.

5. The catheter of claim 4, in which the nitinol comprises cold-worked nitinol and crimped during assembly into the six apertures of the distal portion.

6. The catheter of claim 1, in which each spine of the first, second, and third closed-loop members comprises:
   an elongated structure to provide support for the respective spine;
   a plurality of electrodes coupled to the respective elongated structure, the plurality of electrodes spaced at a predetermined spacing with a respective adjacent electrode on the respective elongate structure and with respect to electrodes on a respective adjacent elongated structure, and the plurality of electrodes comprises from about 30 to about 100 electrodes total, in which a number of electrodes per elongated structure comprises from about 5 to about 15 electrodes; and
   at least one electrode of the plurality of electrodes being radiopaque.

7. The catheter of claim 1, in which each spine of the first, second, and third closed-loop members comprises:
   an elongated structure to provide support for the respective spine, and
   a plurality of electrodes disposed on the respective spine, the plurality of electrodes spaced at a predetermined spacing with respect to a respective adjacent electrode on the respective spine and with respect to electrodes on a respective adjacent spine and the plurality of electrodes comprises from about 30 to about 100 electrodes total, in which a number of electrodes per spine comprises from about 5 to about 15 electrodes.

8. The catheter of claim 7, in which each connector of the first, second, third closed-loop member, the pair of electrodes configured for bi-polar sensing of cardiac signals.

9. The catheter of claim 8, in which said at least a pair of electrodes comprises at least two pairs on each of the first loop connector portion, the second loop connector portion, and the third loop connector portion.

10. The catheter of claim 7, further comprising a pair of referential electrodes disposed on the distal portion.

11. The catheter of claim 1, further comprising at least one magnetic sensor disposed proximate the distal portion so that a location of the distal portion can be determined under a magnetic field.

12. The catheter of claim 1, further comprising at least one impedance location sensor disposed proximate the distal portion of the tubular member to allow a location of the distal portion to be determined based on measured impedance inside a biological subject.

13. The catheter of claim 11, wherein the at least one magnetic sensor comprises three single-axis magnetic sensors.

14. The catheter of claim 1, in which each loop member of the first, second and third closed-loop members is configured to respectively function as a single-axis magnetic coil, so that a location of each loop as referenced to a magnetic field can be determined under the magnetic field and the first, second and third closed-loop members are configured to collectively function as a three axis magnetic sensor.

15. The catheter of claim 1, wherein the puller wire from each of the openings is configured to deflect the distal portion with respect to the longitudinal axis.

16. The catheter of claim 15, wherein the puller wire from each of the openings extend in parallel in the tubular member and are connected to the distal portion so that the puller wires deflect the distal portion in two directions relative to the longitudinal axis.

17. The catheter of claim 16, wherein one of the puller wire of the puller wires deflects the distal portion to define a first radius of curvature with reference to the longitudinal axis and another of the puller wire of the puller wires deflects the distal portion to define a second radius of curvature with reference to the longitudinal axis smaller than the first radius.

* * * * *